(12) United States Patent
Bae et al.

(10) Patent No.: US 8,637,674 B2
(45) Date of Patent: Jan. 28, 2014

(54) PYRAZOLE DERIVATIVES, PREPARATION METHOD THEREOF, AND COMPOSITION FOR PREVENTION AND TREATMENT OF OSTEOPOROSIS CONTAINING SAME

(75) Inventors: Yun Soo Bae, Seongnam-si (KR); Jee Hyun Lee, Seoul (KR); Mi Sun Seo, Seoul (KR); Soo Young Lee, Seoul (KR); Sun Choi, Seoul (KR); Kee In Lee, Daejeon (KR); Hye Rin Bin, Busan (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/393,800

(22) PCT Filed: Sep. 2, 2010

(86) PCT No.: PCT/KR2010/005975
§ 371 (c)(1),
(2), (4) Date: May 15, 2012

(87) PCT Pub. No.: WO2011/028044
PCT Pub. Date: Mar. 10, 2011

(65) Prior Publication Data
US 2012/0232117 A1    Sep. 13, 2012

(30) Foreign Application Priority Data
Sep. 2, 2009  (KR) ..................... 10-2009-0082518

(51) Int. Cl.
*C07D 213/00* (2006.01)
*A61K 31/44* (2006.01)

(52) U.S. Cl.
USPC ........................................ 546/329; 514/340

(58) Field of Classification Search
None
See application file for complete search history.

(56) References Cited

U.S. PATENT DOCUMENTS 5,175,176 A     12/1992  Sasse et al.
5,292,744 A  *  3/1994  Sasse et al. ................. 514/275

FOREIGN PATENT DOCUMENTS

KR    2003-0027709 A    4/2003
WO        93/07138 A1    4/1993

OTHER PUBLICATIONS

CAPLUS 1994:106997.*
CAPLUS 1995:339446.*
Boyle et al., "Osteoclast differentiation and activation," *Nature* 423(6937):337-342, May 15, 2003.
Darden et al., "Osteoclastic Superoxide Production and Bone Resorption: Stimulation and Inhibition by Modulators of NADPH Oxidase," *Journal of Bone and Mineral Research* 11(5):671-675, 1996.
Fraser et al., "Hydrogen Peroxide, but Not Superoxide, Stimulates Bone Resorption in Mouse Calvariae," *Bone* 19(3):223-226, Sep. 1996.
Oikawa et al., "Meldrum's Acid in Organic Synthesis. 2. A General and Versatile Synthesis of β-Keto Esters," *Journal of Organic Chemistry* 43(10):2087-2088, May 1, 1978.
Park et al., "Identification of antitumor activity of pyrazole oxime ethers," *Bioorganic & Medicinal Chemistry Letters* 15(13):3307-3312, Jul. 1, 2005.
Park et al., "Introduction of N-Containing Heterocycles into Pyrazole by Nucleophilic Aromatic Substitution," *Synthetic Communications* 34(9):1541-1550, 2004.
Yang et al., "A New Superoxide-generating Oxidase in Murine Osteoclasts," *Journal of Biological Chemistry* 276(8):5452-5458, 2001.
Yang et al., "Nicotinamide Adenine Dinucleotide Phosphate Oxidase in the Formation of Superoxide in Osteoclasts," *Calcified Tissue International* 63(4):346-350, Oct. 1998.

* cited by examiner

*Primary Examiner* — Janet L Andres
*Assistant Examiner* — Heidi Reese
(74) *Attorney, Agent, or Firm* — Seed IP Law Group PLLC

(57) ABSTRACT

The present invention provides pyrazole derivative compounds and pharmaceutically acceptable salts thereof. The compounds of the present invention have an excellent effect of preventing and treating osteoporosis.

17 Claims, 8 Drawing Sheets

US 8,637,674 B2

PYRAZOLE DERIVATIVES, PREPARATION METHOD THEREOF, AND COMPOSITION FOR PREVENTION AND TREATMENT OF OSTEOPOROSIS CONTAINING SAME

TECHNICAL FIELD

The present invention relates to a novel pyrazole derivative having excellent NADPH oxidase inhibitory activity, a method for preparing the same and a composition for the prevention and treatment of osteoporosis containing the same.

BACKGROUND ART

The process of bone modeling and remodeling plays an important role in development, growth and metabolism of bone. Bone modeling initiates from birth and then continues until adolescence/manhood at which time the skeleton matures to an end of growth of an individual, thus achieving the peak bone mass from between his/her twenties to early-thirties. Since then, a bone remodeling process involving removal and replacement of bone is repeated for about 3 years, during which bone formation and bone resorption are coupled to maintain the balance therebetween. After this period of time, bone formation cannot sufficiently keep up with bone loss occurring due to bone resorption, which eventually results in an about 0.3 to 0.5% annual decrease in bone mass. In particular, women will undergo a significant bone loss of 2 to 3% yearly at the early stage of menopause.

Bone consists mainly of four cell types, namely, osteoblasts, osteoclasts, lining cells and osteocytes. Here, osteoblasts, which are derived from bone marrow stromal cells, are differentiated cells of synthesizing a bone matrix and play a leading part in bone formation, whereas osteoclasts, which are derived from hematopoietic stem cells, play a leading part in bone resorption.

Osteoporosis is a condition in which a calcified bone tissue density is decreased and thus the compact substance of bone is lost gradually, leading to broadening of the marrow cavity. As osteoporosis progresses, bone becomes fragile and consequently bone fractures may readily occur even with a small impact. Bone mass is affected by a variety of factors including genetics, nutrition, hormonal changes, physical exercise and lifestyle habits. Aging, insufficient exercise, being underweight, smoking, low-calcium dietary intake, menopause and ovariectomy are known as pathogenic causes of osteoporosis. Although there is a difference among individuals, it is known that black people exhibit a lower bone resorption level than white people, thus meaning that black people have a higher bone mass. The peak bone mass is generally observed between age 14 and 18, and then the bone mass decreases with aging at a rate of about 1% per year. In particular, bone is continuously decreased from the age of 30 in women and is rapidly reduced due to hormonal changes after menopause. In other words, when reaching the perimenopausal period, a level of estrogen is rapidly decreased. At this time, large numbers of B-lymphocytes are formed as if it happened by interleukin-7 (IL-7), and pre-B cells are accumulated in bone marrow, which consequently leads to an increase in the level of IL-6, thus resulting in an increased activity of osteoclasts and finally a decreased level of bone mass.

As described above, osteoporosis, although showing a difference in terms of disease severity to a certain extent, is inevitable in the aged, especially in post-menopausal women, so osteoporosis and its therapeutic agents have increasingly become the center of interest as the aging population grows in advanced countries. The treatment of bone diseases forms an approximately 130 billion dollar-market throughout the world, which is assumed to grow further. Thus, numbers of worldwide research institutions and pharmaceutical companies have invested heavily in development of therapeutic agents for the treatment of bone diseases. Also recently in Korea, the morbidity of osteoporosis has begun to rapidly soar as the average span of human life comes close to 80 years. According to research recently conducted for local residents, when the research results are normalized in terms of total population, it has been reported that 4.5% of males have osteoporosis and 19.8% of females suffer from the same disease. These results suggest that osteoporosis is a more common disease than diabetes or cardiovascular diseases and when considering the suffering of patients due to fractures or when estimating costs incurred for the treatment of a disease, osteoporosis is a very important public health problem.

Many kinds of substances have been developed hitherto as anti-osteoporosis agents. Among those therapeutic substances, estrogen, which is most commonly used as an anti-osteoporosis agent but whose practical efficacy has not yet been demonstrated, disadvantageously requires life-time administration, and long-term administration thereof may result in adverse side effects such as increased risk of breast cancer or uterine cancer. Alendronate also has problems associated with indefinite understanding of medicinal efficacy, sluggish gastrointestinal absorption, and pathogenesis of inflammation on gastrointestinal and esophageal mucosa. Calcium preparations are known to exhibit superior therapeutic effects with lower adverse side effects but are limited to prevention rather than treatment. Incidentally, vitamin D preparations, such as calcitonin, are known, but efficacy and adverse side effects thereof have not yet been sufficiently investigated. To this end, there is a need for the development of a novel therapeutic agent for the treatment of metabolic bone diseases which exhibits excellent therapeutic effects and a low rate of adverse side effects.

Meanwhile, studies have recently been reported showing that reactive oxygen species (ROS) generated due to oxidative stress are involved in metabolism of bone (Darden, A. G., et al., J. Bone Miner, Res., 11:671-675, 1996; Yang, S., et al., J. Biol. Chem., 276:5452-5458, 2001; Fraser, J. H., et al., Bone 19:223-226, 1996; and Yang, S., et al., Calcif. Tissue Int., 63:346-350, 1998). Further, it is known that bone remodeling is carried out through the relative action between bone-forming osteoblasts and bone-resorbing osteoclasts (OC). Multinuclear osteoclasts are differentiated from a monocyte/macrophage lineage of hematopoietic progenitor cells through a multi-stage process of cell adhesion, proliferation, motility, cell-cell contact and terminal fusion for the formation of multinucleated giant cells. This process is initiated by binding of a receptor activator of nuclear factor-kB ligand (hereinafter, referred to as "RANKL") to a receptor activator of nuclear factor-kB ligand (hereinafter, referred to as "RANK") and is then transmitted through the activation of several signaling cascades. The activated signaling pathway includes NF-KB, extracellular signal-regulated kinase (hereinafter, referred to as "ERK"), c-Jun N-terminal kinase (hereinafter, referred to as "JNK") and p38 mitogen-activated protein (MAP) kinase through a tumor necrosis factor (TNF) receptor-associated factor 6 (hereinafter, referred to as "TRAF6"). Such a signaling event has a direct effect on the modulation of differentiation and action of osteoclasts (Boyle, N. J., et al., Nature, 423:337-342, 2003). Once osteoclasts are differentiated, the resorption of bone is accelerated by ROS generated due to nicotinamide adenine dinucleotide phosphate (NADPH) oxidase. An NADPH oxidase inhibitor leads to a reduction of ROS and bone resorption (Yang, S., et al., Calcif. Tissue Int., 63:346-350, 1998). These results are consistent with the theory suggesting that the generation of ROS in osteoclasts is dependent on the activity of NADPH oxidase and is directly connected with the function of osteoclasts.

Therefore, the inventors of the present application have conducted extensive and intensive studies based on the idea that an anti-osteoporosis agent may be developed by taking advantage of a molecular mechanism which inhibits the activity of RANKL and found that pyrazole derivatives of the present invention exhibit excellent NADPH oxidase inhibitory activity and these compounds may be used for the prevention or treatment of osteoporosis. The present invention has been completed based on these findings.

DISCLOSURE OF THE INVENTION

Technical Problem

Therefore, an object of the present invention is to provide a novel pyrazole derivative having excellent NADPH oxidase inhibitory activity, a method for preparing the same, and a composition for the treatment of osteoporosis containing the same.

It is another object of the present invention to provide a method for preventing or treating osteoporosis, including administering a novel pyrazole derivative of the present invention to a subject in need thereof, and use of a novel pyrazole derivative of the present invention for the preparation of a pharmaceutical formulation for preventing or treating osteoporosis.

Technical Solution

The present invention provides a compound of formula (I):

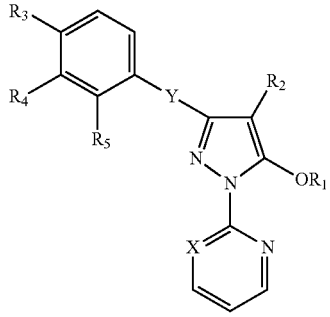

[Formula I]

wherein X represents —CH— or nitrogen;
Y represents —$CH_2$—, —$CH_2CH_2$—, —CH=CH—, —$CH_2$—O— or —O—$CH_2$—;
$R_1$ represents a hydrogen atom, an acetyl group, a tri($C_1$-$C_4$)alkylsilanyl group, a diarylboranyl group or a (t-butoxy)carbamyl group;
$R_2$ represents a hydrogen atom or a $C_1$-$C_4$ alkyl group; and
$R_3$, $R_4$ and $R_5$ each independently represent a hydrogen atom, a hydroxyl group, a halogen atom, a ($C_6$-$C_{10}$)aryl group, a halo($C_1$-$C_3$)alkyl group, a ($C_1$-$C_6$)alkoxy group, a tri($C_1$-$C_4$)alkylsilaneoxy group or a benzodioxolyl group; or alternatively $R_3$ and $R_4$ or $R_4$ and $R_5$ taken together represent —$CH_2$—CH=CH—, —CH=CH—CH=CH— or —CH=CH—CH=CH—$CH_2$—; or a pharmaceutically acceptable salt thereof.

In formula (I) of the present invention, preferred is a compound of formula (I) wherein X represents —CH— or nitrogen; Y represents —$CH_2$—, —$CH_2CH_2$—, —CH=CH—, —$CH_2$—O— or —O—$CH_2$—; $R_1$ and $R_2$ represent a hydrogen atom; and $R_3$, $R_4$ and $R_5$ each independently represent a hydrogen atom, a hydroxyl group, a halogen atom, a ($C_6$-$C_{10}$) aryl group, a halo($C_1$-$C_3$)alkyl group, a ($C_1$-$C_6$)alkoxy group, a tri($C_1$-$C_4$)alkylsilaneoxy group or a benzodioxolyl group; or alternatively $R_3$ and $R_4$ or $R_4$ and $R_5$ taken together represent —$CH_2$—CH=CH— or —CH=CH—CH=CH—; or a pharmaceutically acceptable salt thereof.

In formula (I) of the present invention, more preferred is a compound of formula (I) wherein X represents —CH—; Y represents —CH=CH—, —$CH_2$—O— or —O—$CH_2$—; $R_1$ and $R_2$ represent a hydrogen atom; and $R_3$, $R_4$ and $R_5$ each independently represent a hydrogen atom, a hydroxyl group, a halogen atom, a halo($C_1$-$C_3$)alkyl group, a ($C_1$-$C_6$)alkoxy group or a tri($C_1$-$C_4$)alkylsilaneoxy group; or alternatively $R_3$ and $R_4$ or $R_4$ and $R_5$ taken together represent —CH=CH—CH=CH—; or a pharmaceutically acceptable salt thereof.

In formula (I) of the present invention, when X represents —CH=CH—, the compound may be a trans- or cis-isomer. Preferred is a trans-isomer or a pharmaceutically acceptable salt thereof.

The compound of formula (I) of the present invention is preferably a compound selected from:
3-benzyl-1-(pyridin-2-yl)-1H-pyrazol-5-ol,
3-(o-bromobenzyl)-1-(pyridin-2-yl)-1H-pyrazol-5-ol,
3-(p-methoxybenzyl)-1-(pyridin-2-yl)-1H-pyrazol-5-ol,
3-phenethyl-1-(pyridin-2-yl)-1H-pyrazol-5-ol,
3-(p-chlorobenzyl)-1-(pyridin-2-yl)-1H-pyrazol-5-ol,
3-(phenoxymethyl)-1-(pyridin-2-yl)-1H-pyrazol-5-ol,
3-(naphthalen-3-yloxy)methyl)-1-(pyridin-2-yl)-1H-pyrazol-5-ol,
3-((4-chlorophenoxy)methyl)-1-(pyridin-2-yl)-1H-pyrazol-5-ol,
3-((2,4-dichlorophenoxymethyl)-1-(pyridin-2-yl)-1H-pyrazol-5-ol,
1-(pyridin-2-yl)-3-styryl-1H-pyrazol-5-ol,
3-(4-methoxystyryl)-1-(pyridin-2-yl)-1H-pyrazol-5-ol,
3-(3,4-dimethoxystyryl)-1-(pyridin-2-yl)-1H-pyrazol-5-ol,
3-(3,4-dichlorostyryl)-1-(pyridin-2-yl)-1H-pyrazol-5-ol,
3-(4-i-propylstyryl)-1-(pyridin-2-yl)-1H-pyrazol-5-ol,
3-(4-trifluoromethylstyryl)-1-(pyridin-2-yl)-1H-pyrazol-5-ol,
3-(4-tert-butyldimethylsilyloxystyryl)-1-(pyridin-2-yl)-1H-pyrazol-5-ol,
3-(3-methoxy-4-tert-butyldimethylsilyloxystyryl)-1-(pyridin-2-yl)-1H-pyrazol-5-ol,
3-(3,5-dimethoxy-4-tert-butyldimethylsilyloxystyryl)-1-(pyridin-2-yl)-1H-pyrazol-5-ol,
3-(3-methoxy-4-tert-butyldimethylsilyloxystyryl)-1-(pyridin-2-yl)-1H-pyrazole-5-thiol,
3-(4-hydroxystyryl)-1-(pyridin-2-yl)-1H-pyrazol-5-ol,
3-(3-methoxy-4-hydroxystyryl)-1-(pyridin-2-yl)-1H-pyrazol-5-ol,
3-(3,5-dimethoxy-4-hydroxystyryl)-1-(pyridin-2-yl)-1H-pyrazol-5-ol,
3-(3-methoxy-4-hydroxystyryl)-1-(pyridin-2-yl)-1H-pyrazole-5-thiol, and
4-((E)-2-(5-amino-1-(pyridin-2-yl)-1H-pyrazol-3-yl)vinyl)-2-methoxyphenol; or a pharmaceutically acceptable salt thereof.

The compound of formula (I) of the present invention is more preferably a compound selected from:
3-phenethyl-1-(pyridin-2-yl)-1H-pyrazol-5-ol,
3-(p-chlorobenzyl)-1-(pyridin-2-yl)-1H-pyrazol-5-ol, 3-(phenoxymethyl)-1-(pyridin-2-yl)-1H-pyrazol-5-ol,
3-(naphthalen-3-yloxy)methyl)-1-(pyridin-2-yl)-1H-pyrazol-5-ol,
3-((2,4-dichlorophenoxymethyl)-1-(pyridin-2-yl)-1H-pyrazol-5-ol,
1-(pyridin-2-yl)-3-styryl-1H-pyrazol-5-ol,
3-(4-methoxystyryl)-1-(pyridin-2-yl)-1H-pyrazol-5-ol,
3-(3,4-dimethoxystyryl)-1-(pyridin-2-yl)-1H-pyrazol-5-ol,
3-(3,4-dichlorostyryl)-1-(pyridin-2-yl)-1H-pyrazol-5-ol,
3-(4-trifluoromethylstyryl)-1-(pyridin-2-yl)-1H-pyrazol-5-ol,
3-(4-tert-butyldimethylsilyloxystyryl)-1-(pyridin-2-yl)-1H-pyrazol-5-ol,
3-(4-hydroxystyryl)-1-(pyridin-2-yl)-1H-pyrazol-5-ol, and
3-(3-methoxy-4-hydroxystyryl)-1-(pyridin-2-yl)-1H-pyrazole-5-thiol; or a pharmaceutically acceptable salt thereof.

As used herein, the term "pharmaceutically acceptable salt" refers to a salt commonly used in the pharmaceutical industry, and examples thereof include a salt with an inorganic ion such as calcium, potassium, sodium, or magnesium; a salt with an inorganic acid such as hydrochloric acid, nitric acid, phosphoric acid, bromic acid, iodic acid, perchloric acid, tartaric acid, or sulfuric acid; a salt with an organic acid such as acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, or hydroiodic acid; a salt with sulfonic acid such as methanesulfonic acid, ethanesulfonic acid, benzenesulfonic acid, p-toluenesulfonic acid, or naphthalene sulfonic acid; a salt with amino acid such as glycine, arginine, or lysine; and a salt with amine such as trimethylamine, triethylamine, ammonia, pyridine, or picoline. However, the present invention is not limited thereto.

The compound of formula (I), the above-exemplified compound or a pharmaceutically acceptable salt thereof in accordance with the present invention is capable of preventing or treating osteoporosis by inhibiting the generation of reactive oxygen species. For example, the compound of formula (I), the above-exemplified compound or a pharmaceutically acceptable salt thereof in accordance with the present invention is capable of inhibiting the generation of reactive oxygen species by inhibiting NADPH oxidase.

The compound of formula (I), the above-exemplified compound or d pharmaceutically acceptable salt thereof in accordance with the present invention is capable of treating or preventing osteoporosis by inhibiting the production of osteoclasts. For example, the compound of formula (I), the above-exemplified compound or a pharmaceutically acceptable salt thereof in accordance with the present invention is capable of inhibiting the production of osteoclasts by suppressing differentiation of macrophages into osteoclasts.

The compound of formula (I), the above-exemplified compound or a pharmaceutically acceptable salt thereof in accordance with the present invention is capable of treating or preventing osteoporosis through inhibition of osteoclast formation.

Further, the present invention provides a method for preparing a compound of formula (I), including heating a compound of formula (II) and 2-hydrazinopyridine in a polar organic solvent.

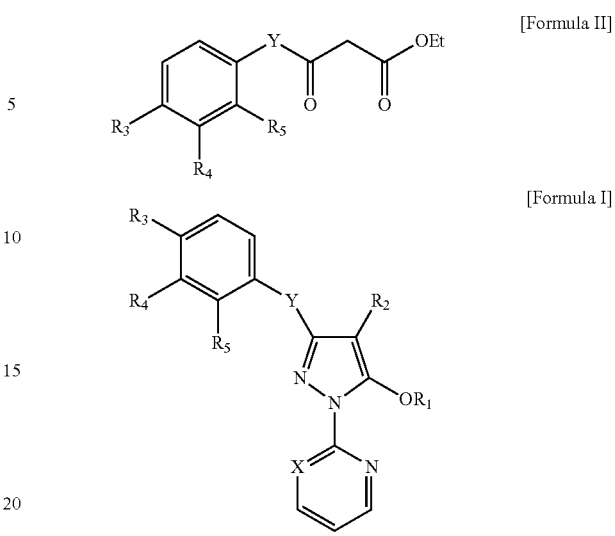

wherein X represents —CH—;
Y represents —CH$_2$—, —CH$_2$CH$_2$—, —CH=CH—, —CH$_2$—O— or —O—CH$_2$—;
R$_1$ represents a hydrogen atom, an acetyl group, a tri(C$_1$-C$_4$)alkylsilanyl group, a diarylboranyl group or a (t-butoxy)carbamyl group;
R$_2$ represents a hydrogen atom or a C$_1$-C$_4$ alkyl group; and
R$_3$, R$_4$ and R$_5$ each independently represent a hydrogen atom, a hydroxyl group, a halogen atom, a (C$_6$-C$_{10}$)aryl group, a halo(C$_1$-C$_3$)alkyl group, a (C$_1$-C$_6$)alkoxy group, a tri(C$_1$-C$_4$)alkylsilaneoxy group or a benzodioxolyl group; or alternatively R$_3$ and R$_4$ or R$_4$ and R$_5$ taken together represent —CH$_2$—CH=CH—, —CH=CH—CH=CH— or —CH=CH—CH=CH—CH$_2$—.

In the preparation method of the present invention, it is more preferable to prepare a compound of formula (I) wherein X represents —CH— or nitrogen; Y represents —CH$_2$—, —CH$_2$CH$_2$—, —CH=CH—, —CH$_2$—O— or —O—CH$_2$—; R$_1$ and R$_2$ represent a hydrogen atom; and R$_3$, R$_4$ and R$_5$ each independently represent a hydrogen atom, a hydroxyl group, a halogen atom, a (C$_6$-C$_{10}$)aryl group, a halo(C$_1$-C$_3$)alkyl group, a (C$_1$-C$_6$)alkoxy group, a tri(C$_1$-C$_4$) alkylsilaneoxy group or a benzodioxolyl group; or alternatively R$_3$ and R$_4$ or R$_4$ and R$_5$ taken together represent —CH$_2$—CH=CH— or —CH=CH—CH=CH—. In the preparation method of the present invention, β-keto ester, which is the compound of formula (II) as used as a starting material, is commercially available or when Y represents —CH$_2$—, —CH$_2$CH$_2$—, —CH$_2$—O— or —O—CH$_2$—, may be prepared according to the method described in J. Org. Chem., Vol. 43, No. 10, 1978, 2087-2088, specifically by reacting a commercially available acyl chloride derivative with Meldrum's acid and heating the resulting product under reflux, in the presence of an ethanol solvent. When Y represents —CH=CH—, the desired compound may be prepared by reacting a cinnamic acid derivative with carbonyl diimidazole (CDI) to activate the acid moiety of the cinnamic acid derivative with acyl imidazolide, and reacting the activated compound with either of ethyl acetate or ethyl thioacetate in the presence of lithium bis(trimethylsilyl)amide (LiHMDS).

In the preparation method of the present invention, 2-hydrazinopyridine is preferably used in an amount of 1.0 to 3 molar equivalents based on 1 mol of the compound (II).

In the preparation method of the present invention, the polar organic solvent is preferably selected from $C_1$-$C_4$ alcohol such as methanol, ethanol, n-propanol, i-isopropanol, n-butanol or t-butanol, acetic acid and a mixture thereof. Ethanol or acetic acid is more preferred.

In the preparation method of the present invention, heating is carried out at a temperature capable of refluxing a solvent. For example, heating is preferably carried out at a temperature of about 100 to about 130° C.

In the preparation method of the present invention, the reaction is preferably carried out for 2 to 72 hours.

Further, the present invention provides a pharmaceutical composition for the prevention or treatment of osteoporosis, containing the compound of formula (I) of the present invention.

As used herein, the term "osteoporosis" refers to a condition in which an absolute quantity of bone with exclusion of a vacant portion (such as marrow cavity) from the entire bone has been decreased; and is intended to encompass senile osteoporosis, post-menopausal osteoporosis, endocrine osteoporosis, congenital osteoporosis, immobilized osteoporosis and post-traumatic osteoporosis.

The composition containing the compound of formula (I), the above-exemplified compound or a pharmaceutically acceptable salt thereof in accordance with the present invention is capable of preventing or treating osteoporosis by inhibiting the generation of reactive oxygen species. For example, the composition containing the compound of formula (I), the above-exemplified compound or a pharmaceutically acceptable salt thereof in accordance with the present invention is capable of inhibiting the generation of reactive oxygen species by inhibiting NADPH oxidase.

The composition containing the compound of formula (I), the above-exemplified compound or a pharmaceutically acceptable salt thereof in accordance with the present invention is capable of treating or preventing osteoporosis by inhibiting the production of osteoclasts. For example, the composition containing the compound of formula (I), the above-exemplified compound or a pharmaceutically acceptable salt thereof in accordance with the present invention is capable of inhibiting the production of osteoclasts by suppressing differentiation of macrophages into osteoclasts.

The composition containing the compound of formula (I), the above-exemplified compound or a pharmaceutically acceptable salt thereof in accordance with the present invention is capable of treating or preventing osteoporosis through inhibition of osteoclast formation.

The pharmaceutical composition of the present invention may contain additives, such as a diluent, a binder, a disintegrant, a lubricant, a pH-adjusting agent, an antioxidant and a solubilizer, which are pharmaceutically acceptable, within the range where effects of the present invention are not impaired.

Examples of the diluent include sugar, starch, microcrystalline cellulose, lactose (lactose hydrate), glucose, D-mannitol, alginate, an alkaline earth metal salt, clay, polyethylene glycol, anhydrous dibasic calcium phosphate, and a mixture thereof; Examples of the binder include starch, microcrystalline cellulose, highly dispersive silica, mannitol, D-mannitol, sucrose, lactose hydrate, polyethylene glycol, polyvinylpyrrolidone (povidone), a polyvinylpyrrolidone copolymer (copovidone), hypromellose, hydroxypropylcellulose, natural gum, synthetic gum, copovidone, gelatin, and a mixture thereof.

Examples of the disintegrant include starches or modified starches such as sodium starch glycolate, corn starch, potato starch, and pregelatinized starch; clays such as bentonite, montmorillonite, and veegum; celluloses such as microcrystalline cellulose, hydroxypropylcellulose, and carboxymethylcellulose; algins such as sodium alginate, and alginic acid; crosslinked celluloses such as croscarmellose sodium; gums such as guar gum, and xanthan gum; crosslinked polymers such as crosslinked polyvinylpyrrolidone (crospovidone); effervescent agents such as sodium bicarbonate and citric acid, and mixtures thereof.

Examples of the lubricant include talc, stearic acid, magnesium stearate, calcium stearate, sodium lauryl sulfate, hydrogenated vegetable oil, sodium benzoate, sodium stearyl fumarate, glyceryl behenate, glyceryl monolaurate, glyceryl monostearate, glyceryl palmitostearate, colloidal silicon dioxide, and mixtures thereof.

Examples of the pH-adjusting agent include acidifying agents such as acetic acid, adipic acid, ascorbic acid, sodium ascorbate, sodium etherate, malic acid, succinic acid, tartaric acid, fumaric acid, and citric acid, and basifying agents such as precipitated calcium carbonate, aqueous ammonia, meglumine, sodium carbonate, magnesium oxide, magnesium carbonate, sodium citrate, and tribasic calcium phosphate.

Examples of the antioxidant include dibutyl hydroxy toluene, butylated hydroxyanisole, tocopherol acetate, tocopherol, propyl gallate, sodium hydrogen sulfite, and sodium pyrosulfite. Examples of the solubilizer that can be used in the immediate-release compartment of the present invention include sodium lauryl sulfate, polyoxyethylene sorbitan fatty acid ester (such as polysorbate), docusate sodium and poloxamer.

In order to prepare a delayed-release formulation, the pharmaceutical composition of the present invention may contain an enteric polymer, a water-insoluble polymer, a hydrophobic compound, and a hydrophilic polymer.

The enteric polymer refers to a polymer which is insoluble or stable under acidic conditions of less than pH 5 and is dissolved or degraded under specific pH conditions of pH 5 or higher. Examples of the enteric polymer include enteric cellulose derivatives such as hypromellose acetate succinate, hypromellose phthalate (hydroxypropylmethylcellulose phthalate), hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate, and methylhydroxyethylcellulose; enteric acrylic acid copolymers such as a styrene/acrylic acid copolymer, a methyl acrylate/acrylic acid copolymer, a methyl acrylate/methacrylic acid copolymer (e.g., Acryl-EZE), a butyl acrylate/styrene/acrylic acid copolymer, and a methyl acrylate/methacrylic acid/octyl acrylate copolymer; enteric polymethacrylate copolymers such as a poly(methacrylic acid/methyl methacrylate) copolymer (e.g., Eudragit L or Eudragit S, manufactured by Evonik, Germany), and a poly(methacrylic acid/ethyl acrylate) copolymer (e.g., Eudragit L100-55, manufactured by Evonik, Germany); enteric maleic acid copolymers such as a vinyl acetate/maleic anhydride copolymer, a styrene/maleic anhydride copolymer, a styrene/maleic monoester copolymer, a vinyl methyl ether/maleic anhydride copolymer, an ethylene/maleic anhydride copolymer, a vinyl butyl ether/maleic anhydride copolymer, an acrylonitrile/methyl acrylate/maleic anhydride copolymer, and a butyl acrylate/styrene/maleic anhydride copolymer; and enteric polyvinyl derivatives such as polyvinyl alcohol phthalate, polyvinylacetal phthalate, polyvinylbutyrate phthalate, and polyvinylacetacetal phthalate.

The water-insoluble polymer refers to a pharmaceutically acceptable water-insoluble polymer which controls the release of a drug. Examples of the water-insoluble polymer include polyvinyl acetate (e.g. Kollicoat SR30D), a water-insoluble polymethacrylate copolymer {e.g. poly(ethyl acrylate-methyl methacrylate) copolymer (such as Eudragit NE30D, a poly(ethyl acrylate-methyl methacrylate-trimethylaminoethyl methacrylate) copolymer (e.g. Eudragit RSPO)}, ethylcellulose, cellulose ester, cellulose ether, cellulose acylate, cellulose diacylate, cellulose triacylate, cellulose acetate, cellulose diacetate, and cellulose triacetate.

The hydrophobic compound refers to a pharmaceutically acceptable water-insoluble material which controls the release of a drug. Examples of the hydrophobic compound include fatty acids and fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as carnauba wax, beeswax and microcrystalline wax; and inorganic materials such as talc, precipitated calcium carbonate, calcium hydrogen phosphate, zinc oxide, titanium oxide, kaolin, bentonite, montmorillonite and veegum.

The hydrophilic polymer refers to a pharmaceutically acceptable water-soluble polymer which controls the release of a drug. Examples of the hydrophilic polymer include saccharides such as dextrin, polydextrin, dextran, pectin and a pectin derivative, alginate, polygalacturonic acid, xylan, arabinoxylan, arabinogalactan, starch, hydroxypropyl starch, amylose and amylopectin; cellulose derivatives such as hypromellose, hydroxypropylcellulose, hydroxymethylcellulose, hydroxyethylcellulose, methylcellulose, and sodium carboxymethylcellulose; gums such as guar gum, locust bean gum, tragacanth, carrageenan, gum acacia, gum arabic, gellan gum and xanthan gum; proteins such as gelatin, casein and zein; polyvinyl derivatives such as polyvinyl alcohol, polyvinylpyrrolidone and polyvinylacetal diethylaminoacetate; hydrophilic polymethacrylate copolymers such as a poly(butyl methacrylate-(2-dimethylaminoethyl)methacrylate-methyl methacrylate) copolymer (e.g. Eudragit E100, manufactured by Evonik, Germany), and a poly(ethyl acrylate-methyl methacrylate-triethylaminoethyl-methacrylate chloride) copolymer (e.g. Eudragit RL and RS, manufactured by Evonik, Germany); polyethylene derivatives such as polyethylene glycol and polyethylene oxide; and carbomer.

In addition, the composition of the present invention may optionally contain pharmaceutically acceptable additives such as various additives selected from colorants and fragrances.

The range of the additive that can be used in the present invention is not limited to the above-mentioned additives, and the additive may be used in a conventional dose which can be appropriately selected by those skilled in the art.

The pharmaceutical composition in accordance with the present invention may be formulated into an oral dosage form such as a powder, a granule, a tablet, a capsule, a suspension, an emulsion, a syrup or an aerosol, or a parenteral dosage form such as an agent for external use, a suppository or a sterile injection, according to a conventional known method.

Further, the present invention provides a method for preventing or treating osteoporosis, including administering the compound of formula (I) of the present invention to a subject including a mammal. As used herein, the term "administering" means the introduction of the composition for the prevention or treatment of osteoporosis in accordance with the present invention to a patient via any appropriate method. The composition for the prevention or treatment of osteoporosis in accordance with the present invention may be administered via any conventional administration route as long as the composition can reach a target tissue. For example, the composition may be administered orally, intraperitoneally, intravenously, intramuscularly, subcutaneously, intradermally, intranasally, intrapulmonary, rectally; intracavitally or intrathecally without being limited thereto.

The composition for the prevention or treatment of osteoporosis in accordance with the present invention may be administered once a day or may be administered at regular time intervals twice or more a day.

The dosage of the compound of formula (I) in accordance with the present invention varies depending on body weight, age, gender, and health state of the patient, diet, administration timing, administration route, excretion rate, and severity of the disease. The compound of formula (I) is administered at a dose of 0.1 to 100 mg/kg/day and preferably at a dose of 10 to 40 mg/kg/day, but may vary depending on sex and age of the patient, severity of the disease, or the like.

Further, the present invention provides a method for inhibiting the generation of reactive oxygen species, including administering the compound of formula (I), the above-exemplified compound or a pharmaceutically acceptable salt thereof in accordance with the present invention to a subject including a mammal.

Further, the present invention provides a method for inhibiting the production of osteoclasts, including administering the compound of formula (I), the above-exemplified compound or a pharmaceutically acceptable salt thereof in accordance with the present invention to a subject including a mammal.

Further, the present invention provides use of the compound of formula (I) of the present invention, for the preparation of a pharmaceutical formulation for the treatment or prevention of osteoporosis.

Further, the present invention provides a health food containing the compound of formula (I) of the present invention. Preferred is a health food for strengthening bone.

Further, the present invention provides a reactive oxygen species-generating inhibitor for inhibiting the generation of reactive oxygen species, containing the compound of formula (I), the above-exemplified compound or a pharmaceutically acceptable salt thereof.

Advantageous Effects

The compound of formula (I) of the present invention has excellent NADPH oxidase inhibitory activity and may also be used for the treatment or prevention of osteoporosis without adverse side effects as exhibited by conventional therapeutic agents.

MODE FOR INVENTION

Figure 1:
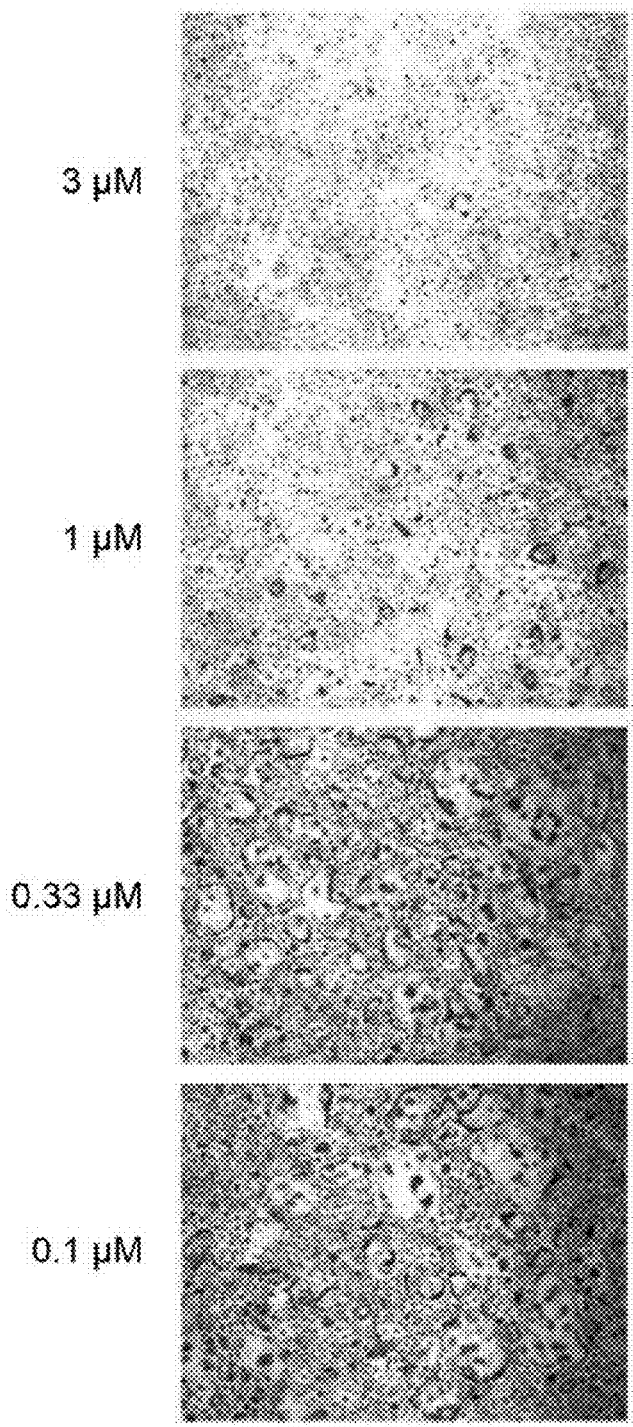
FIGS. 1 to 5 are a view showing an inhibitory effect of compounds of the present invention on osteoclastic differentiation.
Figure 2:
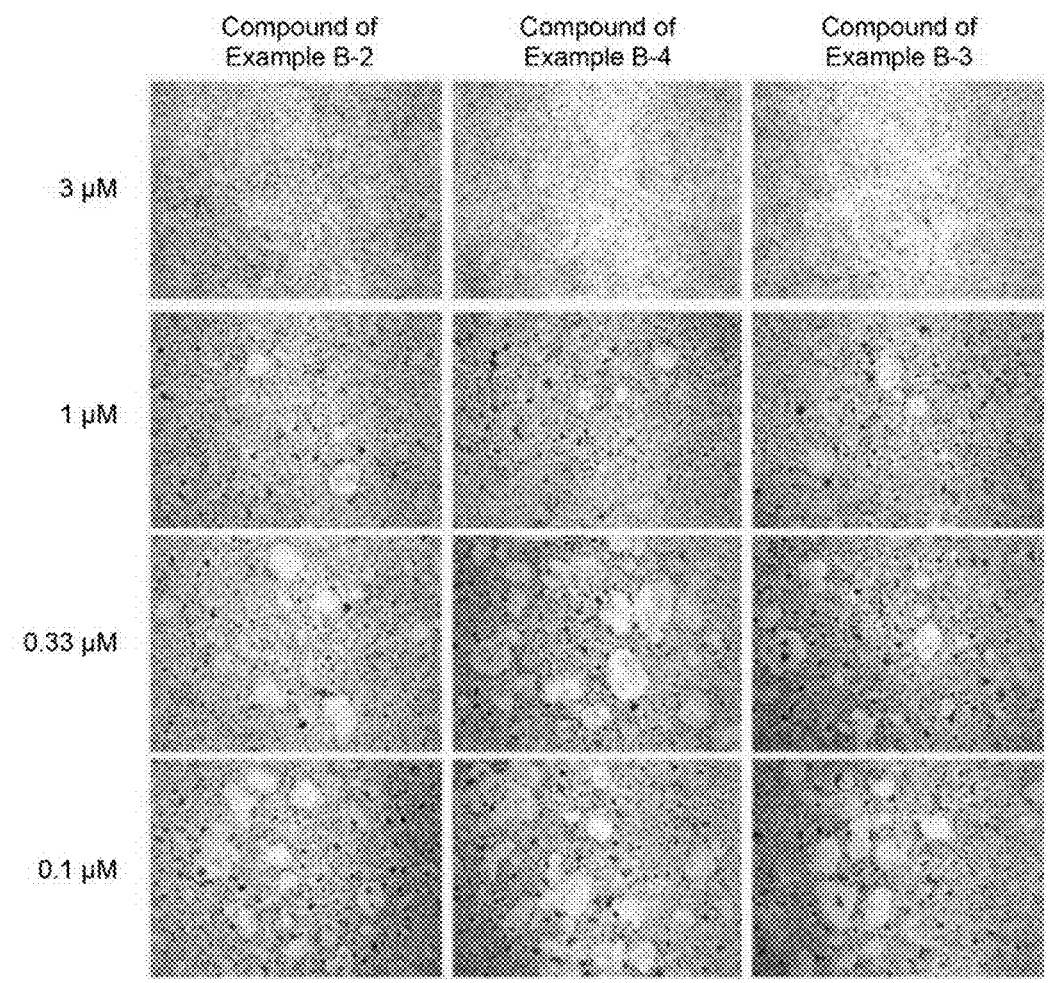
Figure 3:
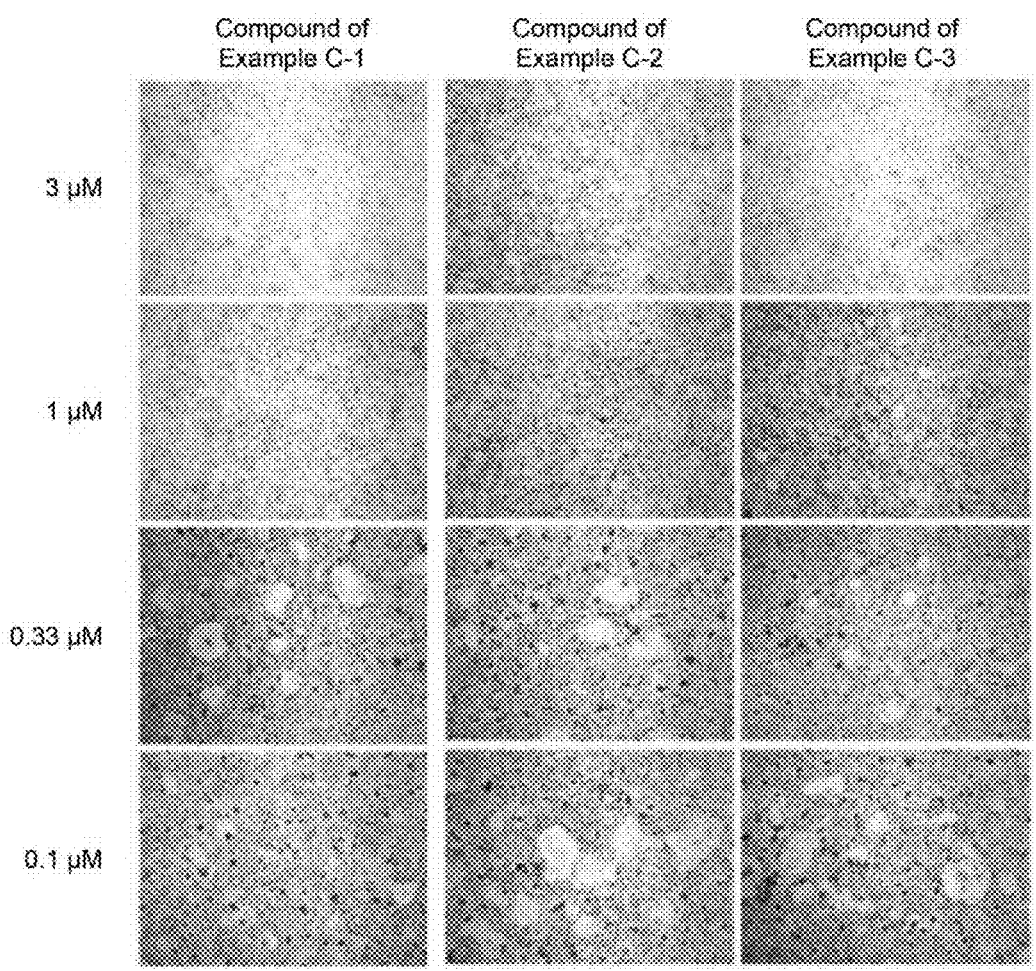
Figure 4:
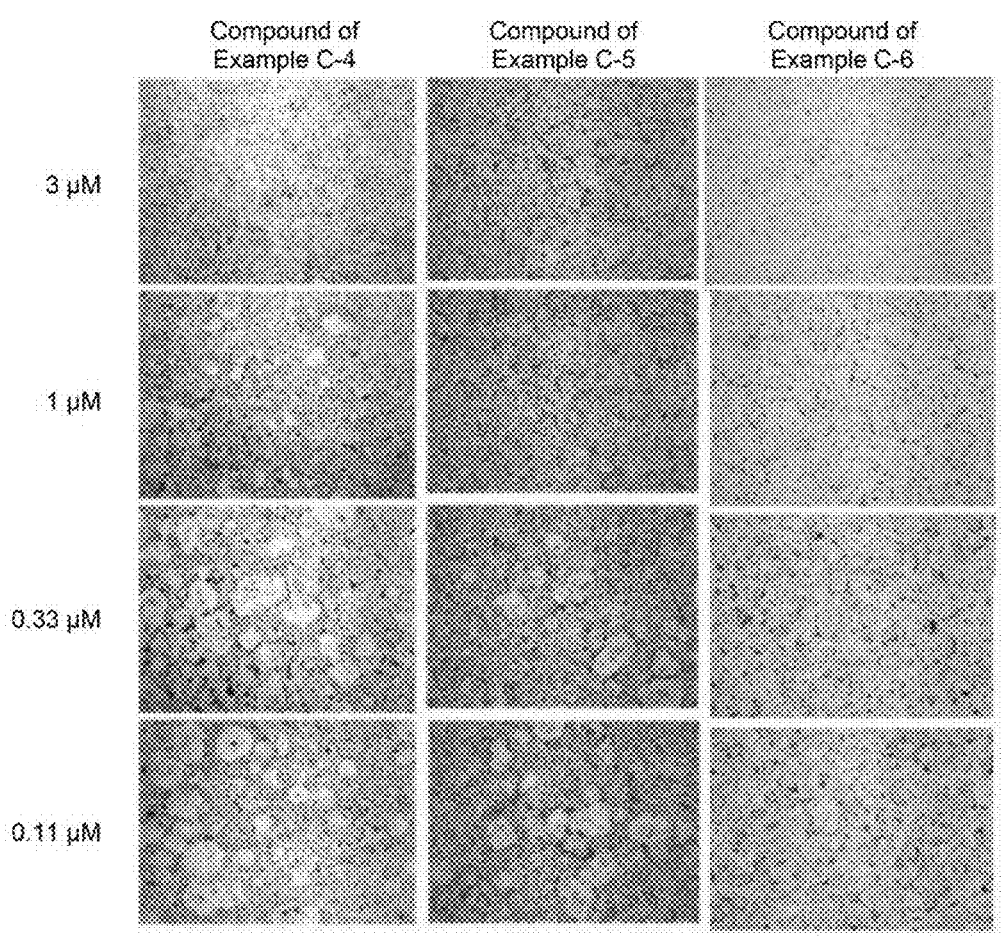
Figure 5:
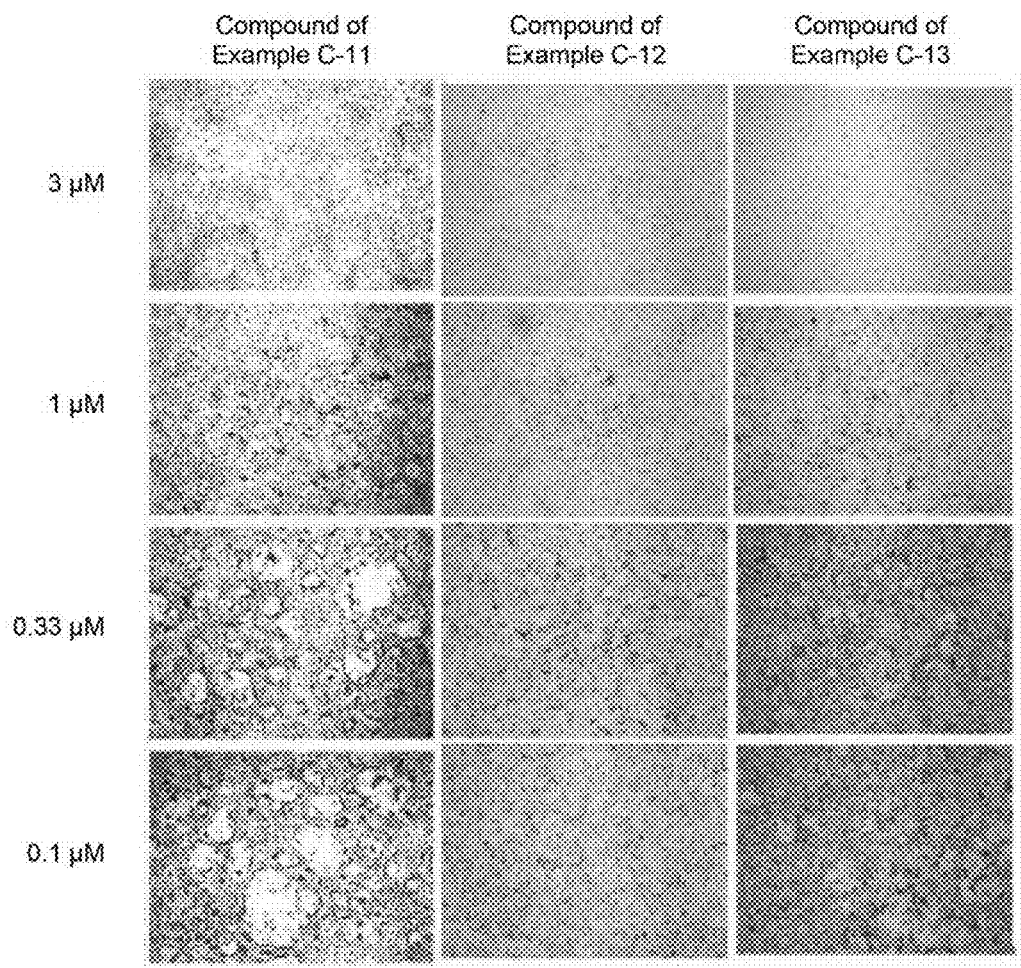

Hereinafter, the present invention will be described in more detail with reference to the following Examples and Experimental Examples. However, it should be understood that the following Examples are provided only for illustrating the present invention and should not be construed as limiting the scope and spirit of the present invention.

A. Introduction of Carbon Spacer Between Pyrazole and Phenyl

The general reaction method of preparing Compound 3 of the present invention in which a carbon spacer has been introduced between the 3-position carbon atom of the pyrazole ring and the phenyl group is as shown in Reaction Scheme 1 below.

[Reaction Scheme 1]

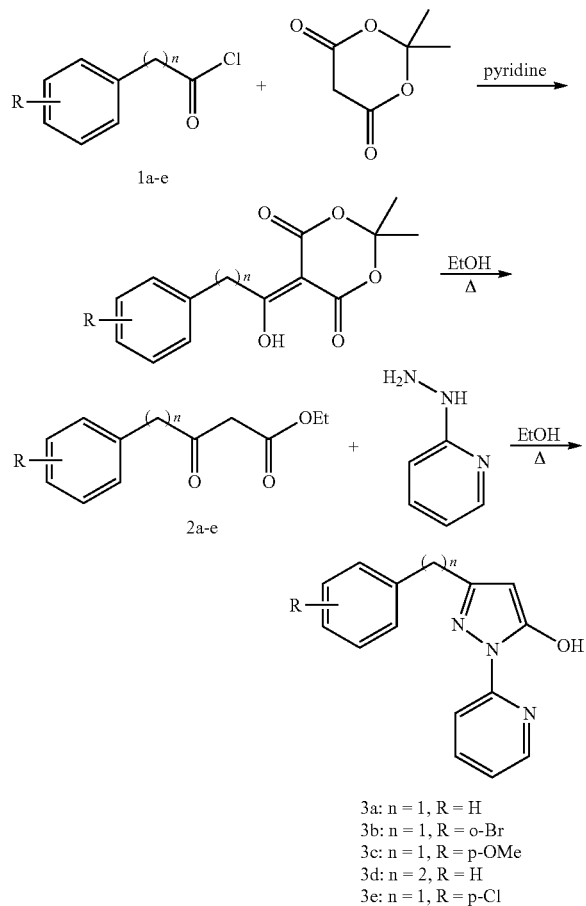

3a: n = 1, R = H
3b: n = 1, R = o-Br
3c: n = 1, R = p-OMe
3d: n = 2, R = H
3e: n = 1, R = p-Cl

As shown in Reaction Scheme 1, β-keto ester (2) used in synthesis of Compound 3 of the present invention may be synthesized by reacting commercially available acyl chloride with Meldrum's acid, adding ethanol to the resulting product, and heating the mixture under reflux, followed by decarboxylation with separation of acetone. Details of the reaction conditions thereof can be found in *J. Org. Chem.*, Vol. 43, No. 10, 1978, 2087-2088.

The desired substance is prepared by subjecting the thus-synthesized β-keto ester (2) and 2-hydrazinopyridine to cyclization under the reaction conditions described in Korean Patent No. 2003-0027709; Min-Sup Park et al., and Synthetic Communications 2004, 34, 1541-1550; Hyun-Ja Park, et al., Bioorganic & Medicinal Chemistry Letters 2005, 15, 3307-3312, or other literature. Here, the reaction solvent is preferably ethanol or acetic acid, the reaction temperature is preferably in the range of 100 to 130° C., and the reaction time is preferably in the range of 2 to 72 hours.

EXAMPLE A-1

Synthesis of 3-benzyl-1-(pyridin-2-yl)-1H-pyrazol-5-ol (3a)

Step 1: Synthesis of ethyl 3-oxo-4-phenylbutanoate (2a)

Meldrum's acid (2.18 g, 15.1 mmol) was charged in a 50 mL round-bottom flask and dissolved in methylene chloride (10 mL). After the temperature was lowered to 0° C., 3 mL of pyridine was gradually added to the flask to which phenylacetyl chloride (1a, 1.95 mL, 14.75 mmol, manufactured by Aldrich) dissolved in 4.5 mL of methylene chloride was then gradually added, followed by stirring at 0° C. for 1 hour and at room temperature for 1 hour.

After completion of the reaction was confirmed by TLC, 10 mL of 2M HCl and ice were added to terminate the reaction. The reaction liquid was washed with 25 mL of saturated brine and then dried over anhydrous sodium sulfate. Thereafter, the solvent was evaporated and concentrated to give an orange crystal. The remaining solvent was thoroughly eliminated by drying under vacuum for 2 hours, and the residue was dissolved in 30 mL of ethanol and a cooling condenser was placed therein, followed by heating under reflux at 70° C. for 2.5 hours. Then, the reaction mixture was concentrated by evaporation to remove ethanol, extracted with ethyl acetate, washed with saturated brine, dried over anhydrous sodium sulfate, concentrated, and then purified by column chromatography [n-Hex:EtOAc=15:1 (v/v)] to afford ethyl 3-oxo-4-phenylbutanoate (2a).

Yield: 71%

$^1$H NMR (300 MHz, CDCl$_3$) δ 7.28 (m, 5H), 4.14 (m, 2H), 3.83 (s, 2H), 3.45 (s, 2H), 1.26 (m, 3H).

Step 2: Synthesis of 3-benzyl-1-(pyridin-2-yl)-1H-pyrazol-5-ol (3a)

Compound 2a (1.03 g, 5.0 mmol) prepared in Step 1 of Example A-1 was charged in a 25 mL round-bottom flask and dissolved in 6 mL of ethanol. A solution of 2-hydrazinopyridine (0.55 g, 5.0 mmol, manufactured by Aldrich) in 5 mL of ethanol at 50° C. was gradually added thereto over 30 minutes, followed by reaction for 1 hour. After completion of the reaction was confirmed by TLC, the reaction solution was concentrated by evaporation, extracted with ethyl acetate, washed with saturated brine, dried over anhydrous sodium sulfate, concentrated, and then purified by column chromatography [n-Hex/EtOAc=3/1 (v/v)] to afford a compound of 3-benzyl-1-(pyridin-2-yl)-1H-pyrazol-5-ol (3a).

Yield: 30.8%

$^1$H NMR (300 MHz, DMSO-d6) δ 12.36 (br, 1H) 8.44-8.41 (m, 1H), 7.98-7.94 (m, 2H), 7.32-7.20 (m, 6H), 5.25 (br, 1H), 3.86 (s, 2H); EIMS m/z (rel intensity) 251 (M+, 100), 159 (82), 129 (11).

EXAMPLE A-2

Synthesis of 3-(o-bromobenzyl)-1-(pyridin-2-yl)-1H-pyrazol-5-ol (3b)

Step 1: Synthesis of ethyl 3-oxo-4-(o-bromo-phenyl)butanoate (2b)

The title compound was prepared in the same manner as in Step 1 of Example A-1, except that an equimolar amount of o-bromo-phenylacetyl chloride (manufactured by Aldrich) was used in place of phenylacetyl chloride.

Yield: 56%

Step 2: Synthesis of 3-(o-bromobenzyl)-1-(pyridin-2-yl)-1H-pyrazol-5-ol (3b)

The title compound was prepared in the same manner as in Step 2 of Example A-1, except that an equimolar amount of ethyl 3-oxo-4-(o-bromo-phenyl)butanoate prepared in Step 1 of Example A-2 was used in place of ethyl 3-oxo-4-phenylbutanoate prepared in Step 1 of Example A-1.

Yield: 19.7%

$^1$H NMR (300 MHz, CDCl$_3$) δ 12.7 (br, 1H) 8.30-8.28 (m, 1H), 7.89-7.82 (m, 2H), 7.62-7.51 (m, 1H), 7.28-7.12 (m, 4H), 5.41 (s, 1H), 4.07 (s, 2H)

EXAMPLE A-3

Synthesis of 3-(p-methoxybenzyl)-1-(pyridin-2-yl)-1H-pyrazol-5-ol (3c)

Step 1: Synthesis of ethyl 3-oxo-4-(p-methoxy-phenyl)butanoate (2c)

The title compound was prepared in the same manner as in Step 1 of Example A-1, except that an equimolar amount of p-methoxy-phenylacetyl chloride (manufactured by Aldrich) was used in place of phenylacetyl chloride.

Yield: 91%

Step 2: Synthesis of 3-(p-methoxybenzyl)-1-(pyridin-2-yl)-1H-pyrazol-5-ol (3c)

The title compound was prepared in the same manner as in Step 2 of Example A-1, except that an equimolar amount of ethyl 3-oxo-4-(p-methoxy-phenyl)butanoate prepared in Step 1 of Example A-3 was used in place of ethyl 3-oxo-4-phenylbutanoate prepared in Step 1 of Example A-1.

Yield: 32.2%

$^1$H NMR (300 MHz, CDCl$_3$) δ 12.75 (br, 1H) 8.25-8.23 (m, 1H), 7.92-7.83 (m, 2H), 7.15-7.11 (m, 3H), 6.87-6.83 (m, 2H), 5.35 (s, 1H), 3.87 (s, 2H), 3.79 (s, 3H).

EXAMPLE A-4

Synthesis of 3-phenethyl-1-(pyridin-2-yl)-1H-pyrazol-5-ol (3d)

Step 1: Synthesis of ethyl 3-oxo-4-phenylpentanoate (2d)

The title compound was prepared in the same manner as in Step 1 of Example A-1, except that an equimolar amount of 3-phenylpropanoyl chloride (manufactured by Aldrich) was used in place of phenylacetyl chloride.

Yield: 86%

Step 2: Synthesis of 3-phenethyl-1-(pyridin-2-yl)-1H-pyrazol-5-ol (3d)

The title compound was prepared in the same manner as in Step 2 of Example A-1, except that an equimolar amount of ethyl 3-oxo-4-phenylpentanoate prepared in Step 1 of Example A-4 was used in place of ethyl 3-oxo-4-phenylbutanoate prepared in Step 1 of Example A-1.

Yield: 85.1%

$^1$H NMR (300 MHz, CDCl$_3$) δ 12.73 (br, 1H) 8.25-8.23 (m, 1H), 7.87-7.84 (m, 2H), 7.32-7.10 (m, 6H), 6.87-6.83 (m, 2H), 5.41 (s, 1H), 5.28 (s, 2H), 2.99-2.91 (m, 2H), 2.90-2.86 (m, 2H).

EXAMPLE A-5

Synthesis of 3-(p-chlorobenzyl)-1-(pyridin-2-yl)-1H-pyrazol-5-ol (3e)

Step 1: Synthesis of ethyl 3-oxo-4-(p-chloro-phenyl)butanoate (2e)

The title compound was prepared in the same manner as in Step 1 of Example A-1, except that an equimolar amount of p-chloro-phenylacetyl chloride (manufactured by Aldrich) was used in place of phenylacetyl chloride.

Yield: 73%

Step 2: Synthesis of 3-(p-chlorobenzyl)-1-(pyridin-2-yl)-1H-pyrazol-5-ol (3e)

The title compound was prepared in the same manner as in Step 2 of Example A-1, except that an equimolar amount of ethyl 3-oxo-4-(p-chloro-phenyl)butanoate prepared in Step 1 of Example A-5 was used in place of ethyl 3-oxo-4-phenylbutanoate prepared in Step 1 of Example A-1.

Yield: 92%

B. Introduction of Ethoxy Spacer Between Pyrazole and Phenyl

The general reaction method of preparing Compound 6 of the present invention in which an ethoxy spacer has been introduced between the 3-position carbon atom of the pyrazole ring and the phenyl group is as shown in Reaction Scheme 2 below.

[Reaction Scheme 2]

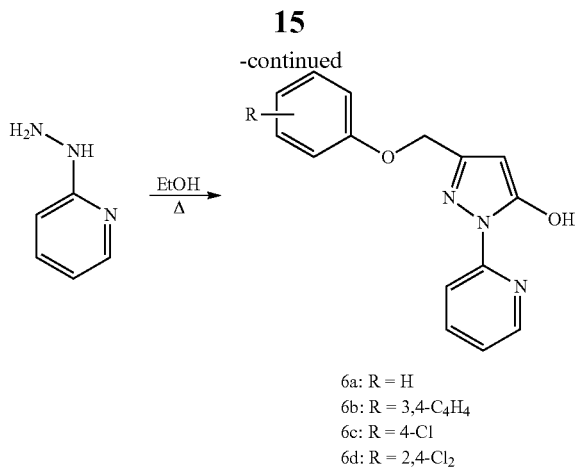

6a: R = H
6b: R = 3,4-C$_4$H$_4$
6c: R = 4-Cl
6d: R = 2,4-Cl$_2$

As shown in Reaction Scheme 2, β-keto ester (5) used in synthesis of Compound 6 of the present invention may be synthesized by reacting commercially available aryloxy acetate with oxalyl chloride to prepare acyl chloride, reacting this acyl chloride with Meldrum's acid, adding ethanol to the resulting product, and heating the mixture under reflux, followed by decarboxylation with separation of acetone. Details of the reaction conditions thereof can be found in *J. Org. Chem.*, Vol. 43, No. 10, 1978, 2087-2088.

The desired substance is prepared by subjecting the thus-synthesized β-keto ester (5) and 2-hydrazinopyridine to cyclization under the reaction conditions described in Korean Patent No. 2003-0027709; Min-Sup Park et al., and Synthetic Communications 2004, 34, 1541-1550; Hyun-Ja Park, et al., Bioorganic & Medicinal Chemistry Letters 2005, 15, 3307-3312, or other literature.

EXAMPLE B-1

Synthesis of 3-(phenoxymethyl)-1-(pyridin-2-yl)-1H-pyrazol-5-ol (6a)

Step 1: Synthesis of ethyl 3-oxo-4-phenoxybutanoate (5a)

The title compound was prepared in the same manner as in Step 1 of Example B-2, except that an equimolar amount of phenoxyacetic acid (manufactured by Fluka) was used in place of 2-naphthalenoxyacetic acid.

Step 2: Synthesis of 3-(phenoxymethyl)-1-(pyridin-2-yl)-1H-pyrazol-5-ol (6a)

Ethyl 3-oxo-4-phenoxybutanoate (5a, 1.2 g, 5.4 mmol) was charged in a 25 mL round-bottom flask and dissolved in 10 mL of ethanol. A solution of 2-hydrazinopyridine (0.55 g, 5.0 mmol) in 5 mL of ethanol at 100° C. was gradually added thereto over 30 minutes, followed by stirring for 20 hours. After completion of the reaction was confirmed by TLC, the reaction solution was concentrated by evaporation, extracted with ethyl acetate, washed with saturated brine, dried over anhydrous sodium sulfate, concentrated, and then purified by column chromatography (n-Hex/EtOAc=9/1 (v/v)) to afford the title compound.
Yield: 60.1%
$^1$H NMR (300 MHz, CDCl$_3$) δ 12.75 (br, 1H) 8.29-8.26 (m, 1H), 7.95-7.85 (m, 2H), 7.35-7.26 (m, 2H), 7.24-7.15 (m, 1H), 7.01-6.93 (m, 3H), 5.72 (s, 1H), 5.04 (s, 2H)

EXAMPLE B-2

Synthesis of 3-((naphthalen-3-yloxy)methyl)-1-(pyridin-2-yl)-1H-pyrazol-5-ol (6b)

Step 1: Synthesis of ethyl 4-(naphthalen-3-yloxy)-3-oxobutanoate (5b)

2-naphthalenoxyacetic acid (4b, 404.4 mg, 2.0 mmol, manufactured by Fluka) was charged in a 25 mL round-bottom flask and dissolved in 28 mL of anhydrous benzene, and oxalyl chloride (0.338 mL, 4.0 mmol, manufactured by Aldrich) was gradually added thereto. A trace of DMF as a catalyst was added to the mixture which was then stirred at room temperature for 2 hours, concentrated, and dissolved in methylene chloride.

After the temperature was lowered to 0° C., a solution of Meldrum's acid (323 mg, 2.24 mmol) in 2 mL of methylene chloride was gradually added to the flask to which 1 mL of pyridine was then gradually added, followed by stirring at room temperature for 18 hours. After completion of the reaction was confirmed by TLC, 1.5 mL of 2M HCl and ice were added to terminate the reaction. The reaction liquid was washed with saturated brine, dried over anhydrous sodium sulfate and then concentrated. The solvent was thoroughly eliminated by drying under vacuum, and the residue was dissolved in 30 mL of ethanol and a cooling condenser was placed therein, followed by heating under reflux at 60° C. for 20 hours. The reaction mixture was concentrated to remove ethanol, extracted with ethyl acetate, washed with saturated brine, dried over anhydrous sodium sulfate, concentrated, and then purified by column chromatography (n-Hex/EtOAc=10/1 (v/v)) to afford ethyl 4-(naphthalen-3-yloxy)-3-oxobutanoate (5b).
Yield: 61%

Step 2: Synthesis of 3-((naphthalen-3-yloxy)methyl)-1-(pyridin-2-yl)-1H-pyrazol-5-ol (6b)

The title compound was prepared in the same manner as in Step 2 of Example B-1, except that an equimolar amount of ethyl 4-(naphthalen-3-yloxy)-3-oxobutanoate prepared in Step 1 of Example B-2 was used in place of ethyl 3-oxo-4-phenoxybutanoate.
Yield: 65.2%
$^1$H NMR (300 MHz, CDCl$_3$) δ 12.76 (br, 1H) 8.29-8.27 (m, 1H), 7.97-7.87 (m, 2H), 7.79-7.74 (m, 3H), 7.49-7.41 (m, 1H), 7.37-7.15 (m, 4H), 5.76 (s, 1H), 5.15 (s, 2H); EIMS m/z (rel intensity) 317 (M+, 100), 174 (99), 106 (7)

EXAMPLE B-3

Synthesis of 3-((4-chlorophenoxy)methyl)-1-(pyridin-2-yl)-1H-pyrazol-5-ol (6c)

Step 1: Synthesis of ethyl 4-(4-chlorophenoxy)-3-oxobutanoate (5c)

The title compound was prepared in the same manner as in Step 1 of Example B-2, except that an equimolar amount of 4-chlorophenoxyacetic acid was used in place of 2-naphthalenoxyacetic acid.
Yield: 73%

Step 2: Synthesis of 3-((4-chlorophenoxy)methyl)-1-(pyridin-2-yl)-1H-pyrazol-5-ol (6c)

The title compound was prepared in the same manner as in Step 2 of Example B-1, except that an equimolar amount of ethyl 4-(4-chlorophenoxy)-3-oxobutanoate prepared in Step 1 of Example B-3 was used in place of ethyl 3-oxo-4-phenoxybutanoate.

Yield: 92.3%

$^1$H NMR (300 MHz, CDCl$_3$) δ 12.77 (br, 1H) 8.30-8.27 (m, 1H), 7.94-7.86 (m, 2H), 7.27-7.17 (m, 4H), 6.96-6.92 (m, 2H), 5.70 (s, 1H), 5.01 (s, 2H)

EXAMPLE B-4

Synthesis of 3-((2,4-dichlorophenoxy)methyl)-1-(pyridin-2-yl)-1H-pyrazol-5-ol (6d)

Step 1: Synthesis of ethyl 4-(2,4-dichlorophenoxy)-3-oxobutanoate (5c)

The title compound was prepared in the same manner as in Step 1 of Example B-2, except that an equimolar amount of 2,4-dichlorophenoxyacetic acid was used in place of 2-naphthalenoxyacetic acid.

Yield: 57%

Step 2: Synthesis of 3-((2,4-dichlorophenoxy)methyl)-1-(pyridin-2-yl)-1H-pyrazol-5-ol (6d)

The title compound was prepared in the same manner as in Step 2 of Example B-1, except that an equimolar amount of ethyl 4-(2,4-dichlorophenoxy)-3-oxobutanoate prepared in Step 1 of Example B-4 was used in place of ethyl 3-oxo-4-phenoxybutanoate.

Yield: 90.2%

$^1$H NMR (300 MHz, CDCl$_3$) δ 12.72 (br, 1H) 8.29-8.27 (m, 1H), 7.91-7.89 (m, 2H), 7.38-7.35 (m, 1H); 7.21-7.13 (m, 2H), 7.04-7.01 (m, 1H), 5.74 (s, 1H), 5.11 (s, 2H); EIMS m/z (rel intensity) 335 (M+, 7), 337 (M+, 5), 174 (100), 107 (9), 80 (2)

C. Introduction of Ethylene Spacer Between Pyrazole and Phenyl

The general reaction method of preparing Compound 9 of the present invention in which an ethylene spacer has been introduced between the 3-position carbon atom of the pyrazole ring and the phenyl group is as shown in Reaction Scheme 3 below.

[Reaction Scheme 3]

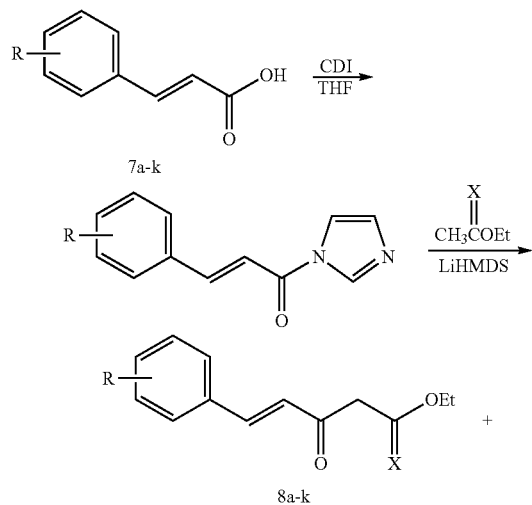

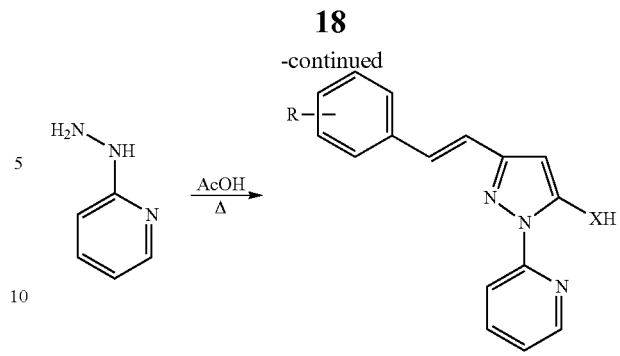

9a: R = H; X = O
9b: R = 4-OMe; X = O
9c: R = 3,4-(OMe)$_2$; X = O
9d: R = 3,4-Cl$_2$; X = O
9e: R = 4-Pr$^i$; X = O
9f: R = 4-CF$_3$; X = O
9g: R = 4-OTBS; X = O
9h: R = 3-OMe-4-OTBS; X = O
9i: R = 3,5-(OMe)$_2$-4-OTBS; X = O
9j: R = 3-OMe-4-OTBS, X = S

As shown in Reaction Scheme 3, Compound 8 used in synthesis of Compound 9 of the present invention was synthesized by activating the acid group of Compound 7 with acyl imidazolide, using Compound 7 which is a commercially available cinnamic acid or cinnamic acid derivative, and carbonyl diimidazole (CDI), followed by reaction with lithioethylacetate (EtOAc, LiHMDS) and ethyl acetate or O-ethyl ethanethioate to prepare β-keto ester of Compound 8. Specifically, β-keto ester having a styrene moiety introduced at the C(3)-position was synthesized by adding lithioethylacetate, obtained by adding LiHMDS to EtOAc in situ, to a solution of acyl imidazolide, obtained from a variety of commercially available cinnamic acids by the action of carbonyl diimidazole (CDI) thereon, without separation and purification. Similarly, β-keto thioester was synthesized using ethyl thioester in place of ethyl acetate.

Thereafter, in the same manner as before, each of β-keto ester and β-keto thioester was subjected to cyclization with 2-hydrazinopyridine, thereby synthesizing Compound 9 which is a 5-hydroxy or 5-mercapto pyrazole derivative.

Among the above-synthesized Compound 9, in the case where R has a silyloxy group, another Compound 9 was also synthesized by an additional reaction of Reaction Scheme 4 below, which involves desilylation with the addition of concentrated hydrochloric acid to MeOH.

[Reaction Scheme 4]

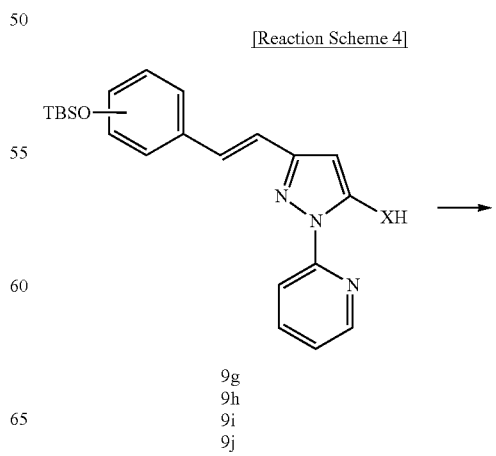

9g
9h
9i
9j

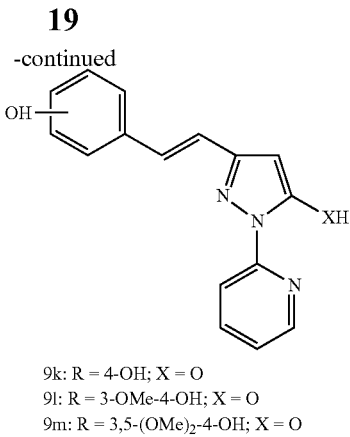

9k: R = 4-OH; X = O
9l: R = 3-OMe-4-OH; X = O
9m: R = 3,5-(OMe)$_2$-4-OH; X = O
9n: R = 3-OMe-4-OH; X = S

EXAMPLE C-1

Synthesis of 1-(pyridin-2-yl)-3-styryl-1H-pyrazol-5-ol (9a)

Step 1: Synthesis of (E)-ethyl-5-phenyl-3-oxopent-4-enoate (8a)

Trans-cinnamic acid (5 mmol, manufactured by Fluka), 1,1'-carbonyl diimidazole (892 mg, 5.5 mmol, manufactured by Aldrich) and tetrahydrofuran (10 mL) were charged in a 25 mL round-bottom flask, followed by stirring at room temperature for 1 hour. 1M lithium bis(trimethylsilyl)amide (10 mL, 10 mmol, manufactured by Aldrich), ethyl acetate (977 μL, 10 mmol), and tetrahydrofuran (10 mL) were added to thereto, followed by stirring at −78° C. for 1 hour. Two solutions were mixed, gradually warmed and stirred at room temperature for 1 hour. A saturated ammonium chloride aqueous solution (50 mL) and ethyl acetate (50 mL) were added thereto, followed by separation of layers into two layers and washing with distilled water and saline. The organic layer was dried over anhydrous sodium sulfate and separated by column chromatography (n-Hex/EtOAc=15/1 (v/v)) to afford Compound 8a.

Yield: 57%

Step 2: Synthesis of 1-(pyridin-2-yl)-3-styryl-1H-pyrazol-5-ol (9a)

2-hydrazinopyridine (161 mg, 1.477 mmol) was added to a solution of (E)-ethyl-5-phenyl-3-oxopent-4-enoate (8a, 355 mg, 1.62 mmol) prepared in Example C-1 in acetic acid (3 mL), followed by stirring under reflux at 60° C. for 30 minutes. Then, the reaction solution was concentrated by distillation under reduced pressure, and ethyl acetate (5 mL) and water (5 mL) were added thereto, followed by extraction with ethyl acetate. The organic layer was dried over anhydrous sodium sulfate and separated by column chromatography (n-Hex/EtOAc=10/1 (v/v)) to afford the title compound.

Yield: 68%

$^1$H NMR (300 MHz, CDCl$_3$) δ 12.86 (br, 1H) 8.29-8.27 (m, 1H), 7.93-7.92 (m, 2H), 7.55-7.49 (m, 2H), 7.43-7.33 (m, 3H), 7.31-7.24 (m, 1H), 7.20-7.14 (m, 1H), 7.11-7.07 (m, 1H), 5.86 (s, 1H); EIMS m/z (rel intensity) 263 (M+, 100), 261 (43), 234 (21), 186 (23), 142 (16), 128 (23), 79 (32)

EXAMPLE C-2

Synthesis of 3-(4-methoxystyryl)-1-(pyridin-2-yl)-1H-pyrazol-5-ol (9b)

Step 1: Synthesis of (E)-ethyl-5-(4-methoxyphenyl-3-oxopent-4-enoate (8b)

The title compound was prepared in the same manner as in Step 1 of Example C-1, except that an equimolar amount of trans-4-methoxy-cinnamic acid (manufactured by Fluka) was used in place of trans-cinnamic acid.

Yield: 94%

Step 2: Synthesis of 3-(4-methoxystyryl)-1-(pyridin-2-yl)-1H-pyrazol-5-ol (9b)

The title compound was prepared in the same manner as in Step 2 of Example C-1, except that an equimolar amount of Compound 8b prepared in Step 1 of Example C-2 was used in place of (E)-ethyl-5-phenyl-3-oxopent-4-enoate prepared in Step 1 of Example C-1.

Yield: 64%

$^1$H NMR (300 MHz, CDCl$_3$) δ 12.84 (br, 1H) 8.27-8.25 (m, 1H), 7.94-7.85 (m, 2H), 7.51-7.43 (m, 2H), 7.18-7.09 (m, 1H), 7.05-7.03 (m, 1H), 6.95-6.86 (m, 3H), 5.82 (s, 1H) 3.84 (s, 3H); EIMS m/z (rel intensity) 293 (M+, 100), 292 (39) 159 (3), 114 (27)

EXAMPLE C-3

Synthesis of 3-(3,4-dimethoxystyryl)-1-(pyridin-2-yl)-1H-pyrazol-5-ol (9c)

Step 1: Synthesis of (E)-ethyl-5-(3,4-dimethoxyphenyl-3-oxopent-4-enoate (8c)

The title compound was prepared in the same manner as in Step 1 of Example C-1, except that an equimolar amount of trans-3,4-dimethoxy-cinnamic acid (manufactured by Fluka) was used in place of trans-cinnamic acid.

Yield: 99%

Step 2: Synthesis of 3-(3,4-dimethoxystyryl)-1-(pyridin-2-yl)-1H-pyrazol-5-ol (9c)

The title compound was prepared in the same manner as in Step 2 of Example C-1, except that an equimolar amount of Compound 8c prepared in Step 1 of Example C-3 was used in place of (E)-ethyl-5-phenyl-3-oxopent-4-enoate prepared in Step 1 of Example C-1.

Yield: 56%

$^1$H NMR (300 MHz, CDCl$_3$) δ 12.87 (br, 1H) 8.30-8.27 (m, 1H), 7.95-7.86 (m, 2H), 7.19-7.14 (m, 1H), 7.09-7.03 (m, 3H), 6.97 (s, 1H), 6.91-6.85 (m, 1H), 5.84 (s, 1H), 3.94 (s, 3H) 3.78 (s, 3H); EIMS m/z (rel intensity) 323 (M+, 100), 188 (14), 120 (89), 95 (7)

EXAMPLE C-4

Synthesis of 3-(3,4-dichlorostyryl)-1-(pyridin-2-yl)-1H-pyrazol-5-ol (9d)

Step 1: Synthesis of (E)-ethyl-5-(3,4-dichlorophenyl-3-oxopent-4-enoate (8d)

The title compound was prepared in the same manner as in Step 1 of Example C-1, except that an equimolar amount of trans-3,4-dichloro-cinnamic acid (manufactured by Fluka) was used in place of trans-cinnamic acid.
Yield: 90%

Step 2: Synthesis of 3-(3,4-dichlorostyryl)-1-(pyridin-2-yl)-1H-pyrazol-5-ol (9d)

The title compound was prepared in the same manner as in Step 2 of Example C-1, except that an equimolar amount of Compound 8d prepared in Step 1 of Example C-4 was used in place of (E)-ethyl-5-phenyl-3-oxopent-4-enoate prepared in Step 1 of Example C-1.
Yield: 54%
$^1$H NMR (300 MHz, CDCl$_3$) δ 12.82 (br, 1H) 8.31-8.29 (m, 1H), 7.92-7.90 (m, 2H), 7.60-7.57 (m, 1H), 7.43-7.40 (m, 1H), 7.35-7.33 (m, 1H), 7.32-7.30 (m, 1H), 7.20-7.16 (m, 1H), 7.03-6.97 (m, 2H), 5.83 (s, 1H); EIMS m/z (rel intensity) 331 (M+, 100), 333 (M+, 68), 186 (22), 120 (48), 79 (68)

EXAMPLE C-5

Synthesis of 3-(4-isopropylstyryl)-1-(pyridin-2-yl)-1H-pyrazol-5-ol (9e)

Step 1: Synthesis of (E)-ethyl-5-(4-isopropylphenyl-3-oxopent-4-enoate (8e)

The title compound was prepared in the same manner as in Step 1 of Example C-1, except that an equimolar amount of trans-4-isopropyl-cinnamic acid (manufactured by Fluka) was used in place of trans-cinnamic acid.
Yield: 69%
$^1$H NMR (300 MHz, CDCl$_3$) δ 7.68 (s, 1H), 7.45-6.93 (m, 10H), 4.21-4.12 (m, 2H), 3.59 (s, 2H), 1.31-1.22 (m, 3H)

Step 2: Synthesis of 3-(4-isopropylstyryl)-1-(pyridin-2-yl)-1H-pyrazol-5-ol (9e)

The title compound was prepared in the same manner as in Step 2 of Example C-1, except that an equimolar amount of Compound 8e prepared in Step 1 of Example C-5 was used in place of (E)-ethyl-5-phenyl-3-oxopent-4-enoate prepared in Step 1 of Example C-1.
Yield: 59%
$^1$H NMR (300 MHz, CDCl$_3$) δ 12.81 (s, 1H), 8.26-8.24 (m, 1H), 7.94-7.83 (m, 2H), 7.45 (d, 2H, J=8.2 Hz), 7.22 (d, 2H, J=8.2 Hz), 7.16-7.11 (m, 1H), 7.06 (s, 1H), 7.03 (s, 1H), 5.83 (s, 1H), 2.96-2.86 (m, 1H), 1.27 (s, 3H), 1.24 (s, 3H);
EIMS (70 eV) m/z (rel intensity) 305 (M+, 100), 290 (40), 276 (91), 262 (91), 212 (41), 186 (66)

EXAMPLE C-6

Synthesis of 3-(4-trifluoromethylstyryl)-1-(pyridin-2-yl)-1H-pyrazol-5-ol (9f)

Step 1: Synthesis of (E)-ethyl-5-(4-trifluoromethylphenyl-3-oxopent-4-enoate (8f)

The title compound was prepared in the same manner as in Step 1 of Example C-1, except that an equimolar amount of trans-4-trifluoromethyl-cinnamic acid (manufactured by Fluka) was used in place of trans-cinnamic acid.
Yield: 52%
$^1$H NMR (300 MHz, CDCl$_3$) δ 7.66-7.56 (m, 5H), 6.88 (d, 1H), 4.29-4.19 (m, 2H), 3.70 (s, 2H), 1.37-1.26 (m, 3H)

Step 2: Synthesis of 3-(4-trifluoromethylstyryl)-1-(pyridin-2-yl)-1H-pyrazol-5-ol (9f)

The title compound was prepared in the same manner as in Step 2 of Example C-1, except that an equimolar amount of Compound 8f prepared in Step 1 of Example C-6 was used in place of (E)-ethyl-5-phenyl-3-oxopent-4-enoate prepared in Step 1 of Example C-1.
Yield: 56%
$^1$H NMR (300 MHz, CDCl$_3$) δ 12.86 (s, 1H), 8.29-8.27 (m, 1H), 7.96-7.87 (m, 2H), 7.57 (s, 4H), 7.20-7.16 (m, 1H), 7.06 (m, 2H), 5.86 (s, 1H)

EXAMPLE C-7

Synthesis of (E)-3-(4-(tert-butyldimethylsilyloxystyryl)-1-(pyridin-2-yl)-1H-pyrazol-5-ol (9g)

Step 1: Synthesis of trans-4-tert-butyldimethylsilyloxy-cinnamic acid 4-hydroxy-cinnamic acid (4.21 g, 25.67 mmol) and imidazole (5.24 g, 77.01 mmol) were charged in a 250 mL round-bottom flask and dissolved in 25 mL of dimethylformamide. Tert-butyldimethylsilyl chloride (8.12 g, 83.90 mmol) was added thereto at 0° C., followed by stirring for 30 minutes. The reaction liquid was concentrated by distillation under reduced pressure and dichloromethane (50 mL) was added thereto, followed by washing with water. The organic layer was dried over anhydrous magnesium sulfate, concentrated and dissolved in tetrahydrofuran (114 mL)/methanol (322 mL), and a 0.00035M potassium carbonate aqueous solution (120 mL) was added thereto, followed by stirring for 1 hour. After being concentrated by distillation under reduced pressure, the resulting solid was filtered, washed with water, and dried under vacuum to afford the title compound.
Yield: 58%
$^1$H NMR (300 MHz, CDCl$_3$) δ 7.74 (d, 1H, J=15.9 Hz), 7.45 (d, 2H, J=8.4 Hz), 6.85 (d, 2H, J=8.7 Hz), 6.32 (d, 1H, J=16.2 Hz), 0.98 (s, 9H), 0.22 (s, 6H)

Step 2: Synthesis of (E)-ethyl-5-(4-tert-butyldimethylsilyloxyphenyl)-3-oxopent-4-enoate (8g)

The title compound was prepared in the same manner as in Step 1 of Example C-1, except that an equimolar amount of trans-4-tert-butyldimethylsilyloxy-cinnamic acid prepared in Step 1 of Example C-7 was used in place of trans-cinnamic acid.
Yield: 93%

Step 3: Synthesis of (E)-3-(4-(tert-butyldimethylsilyloxystyryl)-1-(pyridin-2-yl)-1H-pyrazol-5-ol (9g)

The title compound was prepared in the same manner as in Step 2 of Example C-1, except that an equimolar amount of Compound 8g prepared in Step 2 of Example C-7 was used in place of (E)-ethyl-5-phenyl-3-oxopent-4-enoate prepared in Step 1 of Example C-1.
Yield: 29%
$^1$H NMR (300 MHz, CDCl$_3$) δ 8.27-8.25 (m, 1H), 7.91-7.88 (m, 2H), 7.41-7.37 (m, 2H), 7.17-7.13 (m, 1H), 7.08-7.02 (m, 1H), 6.94-6.81 (m, 3H), 5.82 (s, 1H), 0.99 (s, 9H), 0.22 (s, 6H)

EXAMPLE C-8

Synthesis of (E)-3-(3-methoxy-4-tert-butyldimethyl-silyloxystyryl)-1-(Pyridin-2-yl)-1H-pyrazol-5-ol (9h)

Step 1: Synthesis of trans-3-methoxy-4-tert-butyldimethylsilyloxy-cinnamic acid 3-methoxy-4-hydroxy-cinnamic acid (8 g, 41.2 mmol) and imidazole (8.4 g, 123.6 mmol) were charged in a 500 mL round-bottom flask and dissolved in 30 mL of dimethylformamide. Tert-butyldimethylsilyl chloride (13.04 g, 86.5 mmol) was added thereto at 0° C., followed by stirring for 30 minutes. The reaction liquid was concentrated by distillation under reduced pressure and dichloromethane (200 mL) was added thereto, followed by washing with water.

The organic layer was dried over anhydrous magnesium sulfate, concentrated and dissolved in tetrahydrofuran (180 mL)/methanol (500 mL), and a 0.00035M potassium carbonate aqueous solution (175 mL) was added thereto, followed by stirring for 1 hour. After being concentrated by distillation under reduced pressure, the resulting solid was filtered, washed with water, and dried under vacuum to afford the title compound.

Yield: 93%
$^1$H NMR (300 MHz, CDCl$_3$) δ 7.72 (d, 1H, J=15.9 Hz), 7.07-7.04 (m, 2H), 6.86 (d, 1H, J=8.7 Hz), 6.31 (d, 1H, J=15.9 Hz), 3.84 (s, 3H), 0.99 (s, 9H), 0.17 (s, 6H)

Step 2: Synthesis of (E)-ethyl-5-(3-methoxy-4-tert-butyldimethylsilyloxyphenyl)-3-oxopent-4-enoate (8h)

The title compound was prepared in the same manner as in Step 1 of Example C-1, except that an equimolar amount of trans-3-methoxy-4-tert-butyldimethylsilyloxy-cinnamic acid prepared in Step 1 of Example C-8 was used in place of trans-cinnamic acid.

Yield: 32%

Step 3: Synthesis of (E)-3-(3-methoxy-4-tert-butyldimethylsilyloxystyryl)-1-(pyridin-2-yl)-1H-pyrazol-5-ol (9h)

The title compound was prepared in the same manner as in Step 2 of Example C-1, except that an equimolar amount of Compound 8h prepared in Step 2 of Example C-8 was used in place of (E)-ethyl-5-phenyl-3-oxopent-4-enoate prepared in Step 1 of Example C-1.

Yield: 63%
$^1$H NMR (300 MHz, DMSO) δ 8.55-8.53 (m, 1H), 8.11-8.10 (m, 2H), 7.52 (d, 2H, J=8.5 Hz), 7.44-7.40 (m, 1H), 7.29 (d, 1H, J=16.5 Hz), 6.94-6.87 (m, 3H), 5.93 (s, 1H), 3.25 (s, 2H)

EXAMPLE C-9

Synthesis of (E)-3-(3,5-dimethoxy-4-tert-butyldimethylsilyloxystyryl)-1-(pyridin-2-yl)-1H-pyrazol-5-ol (9i)

Step 1: Synthesis of trans-3,5-dimethoxy-4-tert-butyldimethylsilyloxy-cinnamic acid 3,5-dimethoxy-4-hydroxy-cinnamic acid (3 g, 13.38 mmol) and imidazole (2.73 g, 40.14 mmol) were charged in a 500 mL round-bottom flask and dissolved in 15 mL of dimethylformamide. Tert-butyldimethylsilyl chloride (4.23 g, 28.09 mmol) was added thereto at 0° C., followed by stirring for 1 hour. The reaction liquid was concentrated by distillation under reduced pressure and dichloromethane (50 mL) was added thereto, followed by washing with water. The organic layer was dried over anhydrous magnesium sulfate, concentrated and dissolved in tetrahydrofuran (59 mL)/methanol (167 mL), and a 0.00035M potassium carbonate aqueous solution (62 mL) was added thereto, followed by stirring for 1 hour. After being concentrated by distillation under reduced pressure, the resulting solid was filtered, washed with water, and dried under vacuum to afford the title compound.

Yield: 86%
$^1$H NMR (300 MHz, CDCl$_3$) δ 7.70 (d, 1H, J=15.8 Hz), 6.75 (s, 2H), 6.32 (d, 1H, J=15.8 Hz), 3.83 (s, 6H), 1.01 (s, 9H), 0.14 (s, 6H)

Step 2: Synthesis of (E)-ethyl-5-(3,5-dimethoxy-4-tert-butyldimethylsilyloxyphenyl)-3-oxopent-4-enoate (8i)

The title compound was prepared in the same manner as in Step 1 of Example C-1, except that an equimolar amount of trans-3,5-dimethoxy-4-tert-butyldimethylsilyloxy-cinnamic acid prepared in Step 1 of Example C-9 was used in place of trans-cinnamic acid.

Yield: 44%
$^1$H NMR (300 MHz, CDCl$_3$) δ 7.51 (d, 1H, J=16.1 Hz), 6.76 (s, 2H), 6.67 (d, 1H, J=16.0 Hz), 4.26-4.18 (m, 2H), 3.82 (s, 6H), 3.68 (s, 2H), 1.33-1.25 (m, 3H), 1.00 (s, 9H), 0.14 (s, 6H)

Step 3: Synthesis of (E)-3-(3,5-dimethoxy-4-tert-butyldimethylsilyloxystyryl)-1-(Pyridin-2-yl)-1H-pyrazol-5-ol (9i)

The title compound was prepared in the same manner as in Step 2 of Example C-1, except that an equimolar amount of Compound 8i prepared in Step 2 of Example C-9 was used in place of (E)-ethyl-5-phenyl-3-oxopent-4-enoate prepared in Step 1 of Example C-1.

Yield: 44%
$^1$H NMR (300 MHz, CDCl$_3$) δ 12.83 (bs, 1H), 8.27-25 (m, 1H), 7.92-7.84 (m, 2H), 7.15-6.70 (m, 5H), 5.82 (s, 1H), 3.83 (s, 6H), 1.01 (s, 9H), 0.15 (s, 6H); EIMS (70 eV) m/z (rel intensity) 453 (M+, 24), 396 (100), 381 (92)

EXAMPLE C-10

Synthesis of (E)-3-(3-methoxy-4-tert-butyldimethyl-silyloxystyryl)-1-(pyridin-2-yl)-1H-pyrazole-5-thiol (9j)

Step 1: Synthesis of trans-3-methoxy-4-tert-butyldimethylsilyloxy-cinnamic acid 3-methoxy-4-hydroxy-cinnamic acid (8 g, 41.2 mmol) and imidazole (8.4 g, 123.6 mmol) were charged in a 500 mL round-bottom flask and dissolved in 30 mL of dimethylformamide. Tert-butyldimethylsilyl chloride (13.04 g, 86.5 mmol) was added thereto at 0° C., followed by stirring for 30 minutes. The reaction liquid was concentrated by distillation under reduced pressure and dichloromethane (200 mL) was added thereto, followed by washing with water. The organic layer was dried over anhydrous magnesium sulfate, concentrated and dissolved in tetrahydrofuran (180 mL)/methanol (500 mL), and a 0.00035M potassium carbonate aqueous solution (175 mL) was added thereto, followed by stirring for 1 hour. After being concentrated by distillation under reduced pressure, the resulting solid was filtered, washed with water, and dried under vacuum to afford the title compound.

Yield: 93%

$^1$H NMR (300 MHz, CDCl$_3$) δ 7.72 (d, 1H, J=15.9 Hz), 7.07-7.04 (m, 2H), 6.86 (d, 1H, J=8.7 Hz), 6.31 (d, 1H, J=15.9 Hz), 3.84 (s, 3H), 0.99 (s, 9H), 0.17 (s, 6H)

Step 2: Synthesis of (E)-ethyl-5-(3-methoxy-4-tert-butyldimethylsilyloxyphenyl)-3-oxopent-4-enothioate (8j)

The title compound was prepared in the same manner as in Step 1 of Example C-1, except that an equimolar amount of each of trans-3-methoxy-4-tert-butyldimethylsilyloxy-cinnamic acid prepared in Step 1 of Example C-10 and ethyl thioacetate was used in place of trans-cinnamic acid and ethyl acetate.

Yield: 60%

$^1$H NMR (300 MHz, CDCl$_3$) δ 12.56 (s, 1H), 7.43 (d, 1H, J=15.8 Hz), 7.05-6.98 (m, 3H), 6.22 (d, 1H, J=15.8 Hz), 5.55 (s, 1H), 3.83 (s, 3H), 2.97 (q, 2H, J=7.4 Hz), 1.32 (t, 3H, J=7.4 Hz), 0.99 (s, 9H), 0.16 (s, 6H)

Step 3: Synthesis of (E)-3-(3-methoxy-4-tert-butyldimethylsilyloxystyryl)-1-(pyridin-2-yl)-1H-pyrazole-5-thiol (9j)

The title compound was prepared in the same manner as in Step 2 of Example C-1, except that an equimolar amount of Compound 8j prepared in Step 2 of Example C-10 was used in place of (E)-ethyl-5-phenyl-3-oxopent-4-enoate prepared in Step 1 of Example C-1.

Yield: 59%

$^1$H NMR (300 MHz, CDCl$_3$) δ 12.82 (bs, 1H), 8.27-8.24 (m, 1H), 7.93-7.83 (m, 2H), 7.16-6.81 (m, 6H), 5.82 (s, 1H), 3.84 (s, 3H), 1.00 (s, 9H), 0.17 (s, 6H); EIMS (70 eV) m/z (rel intensity) 423 (M+—CH$_3$, 27), 366 (87), 351 (100), 322 (7), 258 (5), 231 (10), 186 (10)

EXAMPLE C-11

Synthesis of 3-(4-hydroxystyryl)-1-(pyridin-2-yl)-1H-pyrazol-5-ol (9k)

(E)-3-(4-(tert-butyldimethylsilyloxystyryl)-1-(pyrimidin-2-yl)-1H-pyrazol-5-ol (9 g, 545 mg, 1.38 mmol) prepared in Example C-7 was dissolved in methanol (5 mL) and concentrated hydrochloric acid (1 mL) was added thereto, followed by stirring at room temperature for 24 hours. The resulting solid was filtered and dried under vacuum to afford the title compound.

Yield: 93%

$^1$H NMR (300 MHz, CD$_3$OD) δ 8.42-8.40 (m, 1H), 8.16-8.09 (m, 1H), 7.98-7.92 (m, 1H), 7.44-7.40 (m, 2H), 7.28-7.23 (m, 1H), 7.18 (s, 1H), 6.83-6.78 (m, 3H); EIMS m/z (rel intensity) 279 (M+, 100), 186 (12), 121 (15), 79 (50).

EXAMPLE C-12

Synthesis of 3-(3-methoxy-4-hydroxystyryl)-1-(pyridin-2-yl)-1H-pyrazol-5-ol (9l)

The title compound was prepared in the same manner as in Example C-11, except that an equimolar amount of Compound 9h prepared in Example C-8 was used in place of Compound 9g.

Yield: 95%

$^1$H NMR (300 MHz, DMSO-d6) δ 9.29 (bs, 1H), 8.46-8.43 (m, 1H), 8.06-7.99 (m, 2H), 7.32-7.15 (m, 3H), 7.04-6.77 (m, 3H), 5.85 (bs, 1H), 3.83 (s, 3H)

EXAMPLE C-13

Synthesis of 3-(3,5-dimethoxy-4-hydroxystyryl)-1-(pyridin-2-yl)-1H-pyrazol-5-ol (9m)

The title compound was prepared in the same manner as in Example C-11, except that 1.201 mmol of Compound 9i prepared in Example C-9 was used in place of Compound 9g.

Yield: 94%

$^1$H NMR (300 MHz, DMSO-d6) δ 8.37-8.36 (m, 1H), 7.99-7.87 (m, 2H), 7.27-7.23 (m, 1H), 7.12 (d, 1H, J=16.4 Hz), 6.86 (d, 1H, J=16.4 Hz), 6.79 (s, 2H), 5.78 (s, 1H), 3.72 (s, 6H)

EXAMPLE C-14

Synthesis of 3-(3-methoxy-4-hydroxystyryl)-1-(pyridin-2-yl)-1H-pyrazole-5-thiol (9n)

The title compound was prepared in the same manner as in Example C-13, except that an equimolar amount of Compound 9j prepared in Example C-10 was used in place of Compound 9i.

Yield: 96%

$^1$H NMR (300 MHz, CDCl$_3$) δ 8.28-8.25 (m, 1H), 7.90-7.87 (m, 2H), 7.17-6.87 (m, 6H), 5.82 (s, 1H), 3.93 (s, 3H); EIMS (70 eV) m/z (rel intensity) 309 (M+—OH, 100), 294 (10), 248 (7), 186 (10), 131 (17)

D. Introduction of Ethylene Spacer Between Pyrazole and Phenyl

The general reaction method of preparing Compound 11 of the present invention in which an amino group has been introduced at the 5-position carbon atom of the pyrazole ring is as shown in Reaction Scheme 5 below.

[Reaction Scheme 5]

EXAMPLE D

Synthesis of 4-((E)-2-(5-amino-1-(pyridin-2-yl)-1H-pyrazol-3-yl)vinyl)-2-methoxyphenol (11)

Step 1: Synthesis of (E)-5-(4-hydroxy-3-methoxyphenyl)-3-oxopent-4-enenitrile (10)

Trans-ethyl(4-hydroxy-3-methoxy)cinnamate (222 mg, 1 mmol, manufactured by Fluka), acetonitrile (156 μL, 3 mmol), 1M lithium bis(trimethylsilyl)amide (3 mL, 3 mmol) and tetrahydrofuran (3 mL) were stirred at room temperature for 30 minutes. A saturated ammonium chloride aqueous solution (15 mL) and ethyl acetate (10 mL) were added thereto, followed by separation of layers into two layers and washing with distilled water and saline. The organic layer was dried over anhydrous sodium sulfate and separated by column chromatography (n-Hex/EtOAc=3/1 (v/v)) to afford Compound 10.

Yield: 58%

$^1$H NMR (300 MHz, CDCl$_3$) δ 7.62 (d, 1H, J=15.8 Hz), 7.16 (d, 1H, J=8.3 Hz), 7.07 (s, 1H), 6.96 (d, 1H, J=8.2 Hz), 6.73 (d, 1H, J=15.8 Hz), 6.01 (s, 1H), 3.95 (s, 3H), 3.68 (s, 2H)

Step 2: Synthesis of 4-((E)-2-(5-amino-1-(pyridin-2-yl)-1H-pyrazol-3-yl)vinyl)-2-methoxyphenol (11)

2-hydrazinopyridine (62 mg, 0.57 mmol) was added to a solution of Compound 10 (113 mg, 0.520 mmol) synthesized in Step 1 of Example D in acetic acid (3 mL), followed by stirring under reflux at 120° C. for 30 minutes. The reaction solution was concentrated by distillation under reduced pressure, and ethyl acetate (5 mL) and water (5 mL) were added thereto, followed by extraction with ethyl acetate. The organic layer was dried over anhydrous sodium sulfate and then separated by column chromatography (n-Hex/EtOAc=3/1 (v/v)) to afford the title compound.

Yield: 20%

$^1$H NMR (300 MHz, CDCl$_3$) δ 8.31-8.30 (m, 1H), 7.97 (d, 1H, J=8.4 Hz), 7.80-7.74 (m, 1H), 7.09-6.87 (m, 6H), 5.98 (bs, 2H), 5.73 (s, 1H), 3.90 (s, 3H)

EXPERIMENTAL EXAMPLE 1

Inhibitory Effects of Inventive Compounds on Generation of Reactive Oxygen Species A kidney was isolated from a rat (*Rattus norvegicus*) and washed with phosphate buffered saline (PBS). The tissue was soaked in 20 mL of PBS buffer containing a protease inhibitor (Aprotinin 1 μg/mL-USB 11388, Leupeptin 1 μg/mL-USB-18413), finely disrupted using a mixer, and then transferred to a 50 mL conical tube (SPL 50050), followed by centrifugation at 10000 g for 10 minutes (MF-600 plus, Hanil) to sediment the undisrupted tissue. The supernatant was separated and collected in a fresh tube. The tube was placed in ice and subjected to sonication about 4 times each cycle for 30 seconds until the supernatant became clear (Branson Digital Sonifier, Model CE Converter 102C). The supernatant was transferred to a high-speed centrifugation tube (Beckman 331372) and then centrifuged at 100000 g for 1 hour (Optima™ L-90 K Preparative Ultracentrifuge, SW41Ti rotor, Beckman). After the supernatant was discarded, the remaining pellet was washed once with cold PBS and dissolved in 500 μL of cold PBS containing a protease inhibitor to obtain a murine kidney membrane.

Reactive oxygen species generated in the thus-obtained kidney membrane was analyzed by a lucigenin-based assay. [Since lucigenin, when it is in a normal state (reduced form), does not generate luminescence, but when it is converted into an oxidized form by the action of reactive oxygen species, generates luminescence, the amount of reactive oxygen species is measured by analyzing the intensity of the generated luminescence using a luminometer].

Specifically, each of the compounds synthesized in Examples of the present invention (40 μM, 10 μM, 2.5 μM, 0.625 μM, and 0 μM) was placed in a luminescence assay microplate, and the isolated kidney membrane and lucigenin were sequentially added thereto, followed by incubation at 37° C. for 10 minutes. Then, the intensity of luminescence was measured in a luminometer (MicroLumatPlus LB96V Microplate Luminometer, Berthold) to assay the generation of reactive oxygen species in the murine kidney membrane, followed by calculating an EC$_{50}$ value of the inventive compounds.

TABLE 1

| Compound No. | EC$_{50}$(μM) |
|---|---|
| 3d | 10 |
| 3e | 1.5 |
| 6a | 7.5 |
| 6b | 0.4 |
| 6d | 1.8 |
| 9a | 0.5 |
| 9b | 0.5 |
| 9c | 0.6 |
| 9d | 1.7 |
| 9f | 0.5 |
| 9g | 0.9 |
| 9k | 1.5 |

As shown in Table 1, the compounds of the present invention were capable of inhibiting the generation of reactive oxygen species even at a low dose. Therefore, it can be seen from the above experiment that the compounds of the present invention have an excellent inhibitory effect on the generation of reactive oxygen species.

EXPERIMENTAL EXAMPLE 2

Inhibitory Effects of Inventive Compounds on Osteoclast Differentiation

Bone marrow cells were collected from 4 to 5-week old male mice (C57BL/6J).

Specifically, mice were sacrificed by cervical dislocation, and femur and tibia were extracted while removing muscles adhered around the bone with scissors and soaked in phosphate buffered saline (PBS). A 1 mL syringe filled with α-minimal essential medium (α-MEM) was put into one end of the femur and tibia from which bone marrow cells were then harvested.

The bone marrow cells were cultured to obtain macrophages. Specifically, the above-obtained bone marrow cells were placed in a 50 mL tube and centrifuged at 1500 rpm for 5 minutes. The supernatant was discarded, and a 3:1 mixture of a Gey's solution and PBS was added, followed by maintenance at room temperature for about 2 to 3 minutes. After another centrifugation (1500 rpm, 5 minutes), the supernatant was discarded, α-MEM was added, followed by stirring, and then the cells were cultured in a 10 cm cell culture dish at 37° C. for 24 hours. After performing the 3$^{rd}$ centrifugation (1500 rpm, 5 minutes), the supernatant was discarded, a culture medium and a macrophage differentiation factor, rhM-CSF (30 ng/mL) were added, and then the cells were cultured in a 10 cm cell culture dish at 37° C. for 3 days. After 3 days, macrophages adhered to the dish were scraped and collected in a tube, followed by centrifugation (1500 rpm, 5 minutes).

The macrophages were cultured to induce cellular differentiation thereof into osteoclasts. Specifically, the above-obtained macrophages were aliquoted at a density of $2 \times 10^4$ cells/well in a 48-well cell culture dish, followed by culture for 24 hours. rhM-CSF (30 ng/mL) and an osteoclast differentiation factor, RANKL (200 ng/mL) were added to the culture medium, followed by culture to induce cellular differentiation thereof into osteoclasts. At this time, as for an experimental group, each of the compounds synthesized in Examples of the present invention (compounds synthesized in Examples A-3, B-2 to B-4, C-1 to C-6, and C-11 to C-13) at a varying concentration of 3 µM, 1 µM, 0.33 µM and 0.1 µM was added to the culture medium, and as for a control group, DMSO was added at a varying concentration of 3 µM, 1 µM, 0.33 µM and 0.1 µM.

After 24 hours, the culture medium in the 48-well cell culture dish was removed and replaced with a fresh medium, followed by cell culture at 37° C. while exchanging the culture medium every two days.

After further culturing for 5 days from the day on which each of the compounds of the present invention was added to the medium, the medium to which each of the compounds of the present invention was added and the control group medium were respectively fixed in a 3.7% formalin solution, subjected to tartrate resistant acid phosphatase (TRAP) staining, and examined under a light microscope. The results are shown in FIG. 1. Specifically, the TRAP staining was carried out as follows: The cells were fixed in 3.7% formaldehyde at room temperature for 15 minutes, and washed twice with distilled water. A staining solution, which was prepared by mixing acetate, Fast Gargnet GBC base, naphthol AS-BI phosphate, sodium nitride and tartrate in the ratio described in the instructions attached to an Acid Phosphatase, Leukocyte (TRAP) Kit™ (Sigma Co.), was added at a dose of 200 µL/well, followed by reacting with the cells at 37° C. for 20 minutes.

Figure 6:
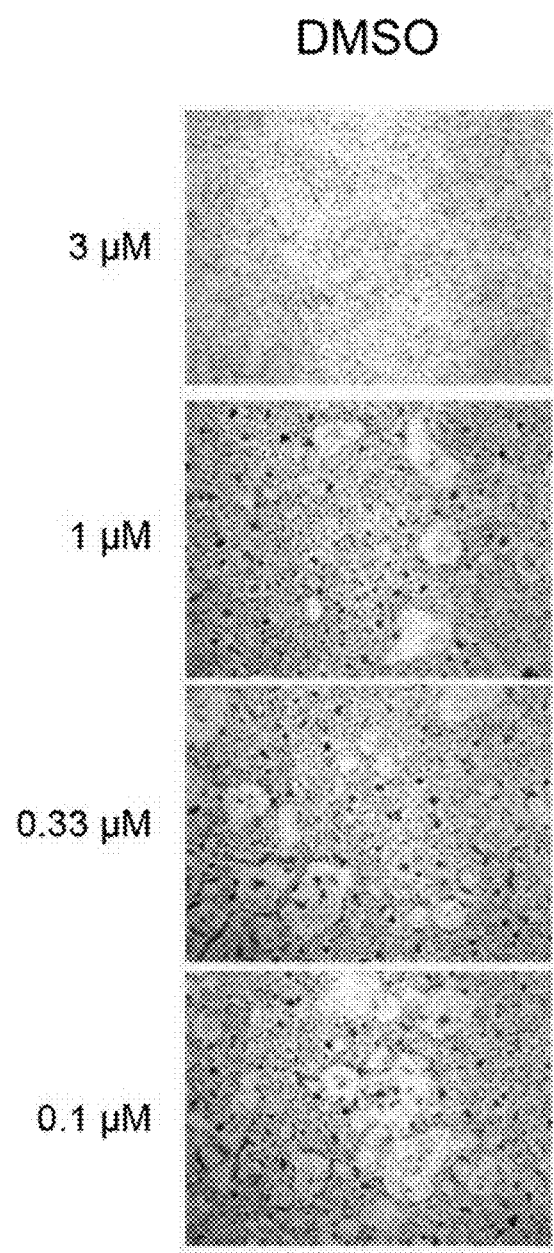
FIG. 6 is a view showing differentiation of a control group into osteoclasts.

The results observed for macrophages cultured in the medium to which each of the compounds synthesized in Examples of the present invention was added are shown in FIGS. 1 to 5. The results observed for macrophages cultured in the medium to which DMSO was added are shown in FIG. 6.

As shown in FIGS. 1 to 6, the control group with the addition of DMSO exhibited differentiation of macrophages into osteoclasts, whereas macrophages of the medium with the addition of compounds of the present invention did not exhibit normal differentiation thereof into osteoclasts.

Further, as the concentration of the compounds of the present invention became higher such as 0.1 µM, 0.33 µM, 1 µM and 3 µM, cellular differentiation into osteoclasts was further suppressed.

Accordingly, it can be seen that the compounds of the present invention inhibit differentiation of macrophages into osteoclasts in a dose-dependent fashion.

EXPERIMENTAL EXAMPLE 3

Inhibitory Effects of Inventive Compounds on LPS-Induced Osteolysis

In order to investigate inhibitory effects of the inventive compounds on lipopolysaccharide (LPS)-induced osteolysis in a bone-loss mouse model, 6-week old C57BL/6J male mice were divided into Control group 1, Control group 2 and Experimental group 1.

Mice were anesthetized, followed by making a 1 cm skin incision of a cranial median section and a collagen sponge with a size of 0.5 mm×0.5 mm was put into the incision site. For Control group 1, PBS alone was infused into the sponge; for Control group 2, 12.5 mg/kg of LPS was infused; and for Experimental group 1, 12.5 mg/kg of LPS and 20 mg/kg of each of the compounds prepared in Examples (A-3, C-11) were infused.

Thereafter, the incised skins were sutured, and after 5 days, the murine cranium was excised, fixed in 3.7% formalin for 24 hours and then subjected to decalcification with the addition of a 0.5M EDTA solution. The decalcified cranium was embedded in paraffin to prepare a paraffinized block which was then cut using a microtome. Then, the cut block was subjected to hematoxylin and eosin staining (H&E staining), followed by microscopic examination. The results are shown in FIGS. 7 and 8.

Figure 7:
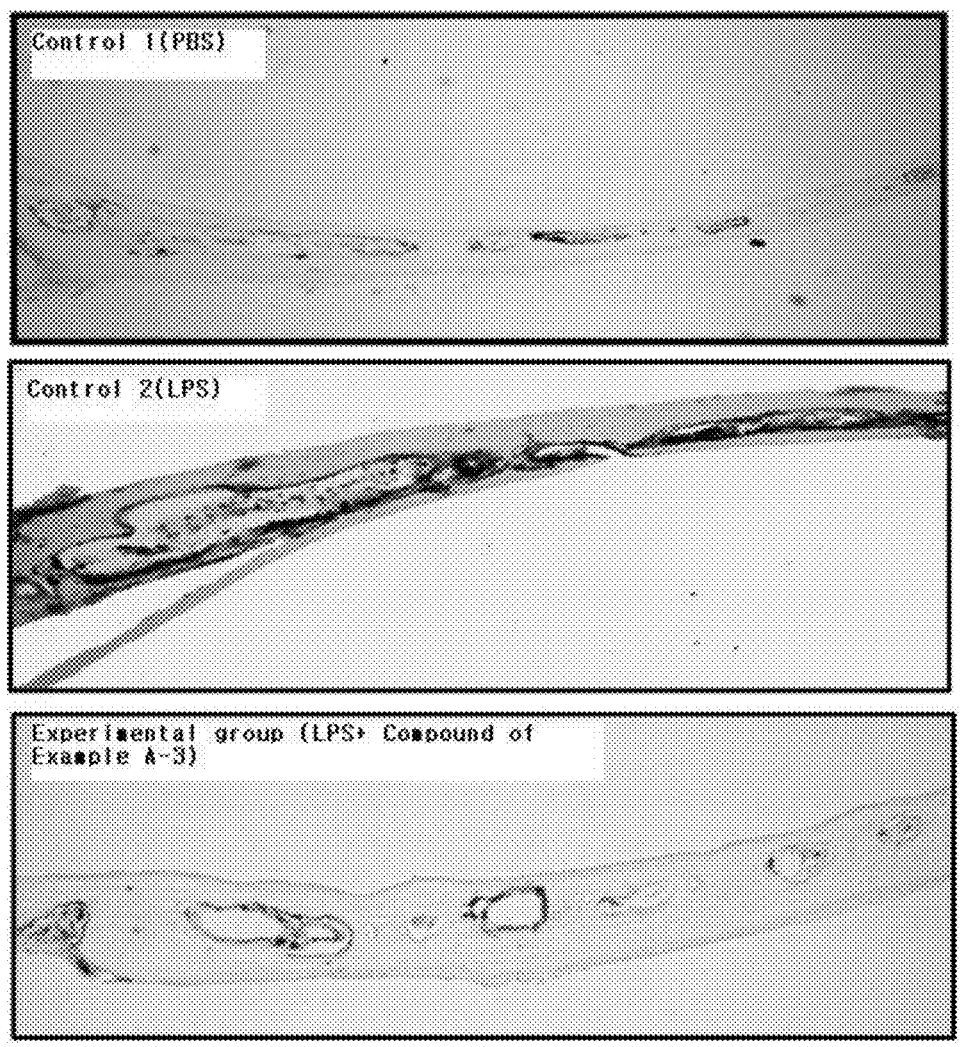
FIGS. 7 and 8 are a view showing an inhibitory effect of compounds of the present invention on LPS-induced osteolysis.
Figure 8:
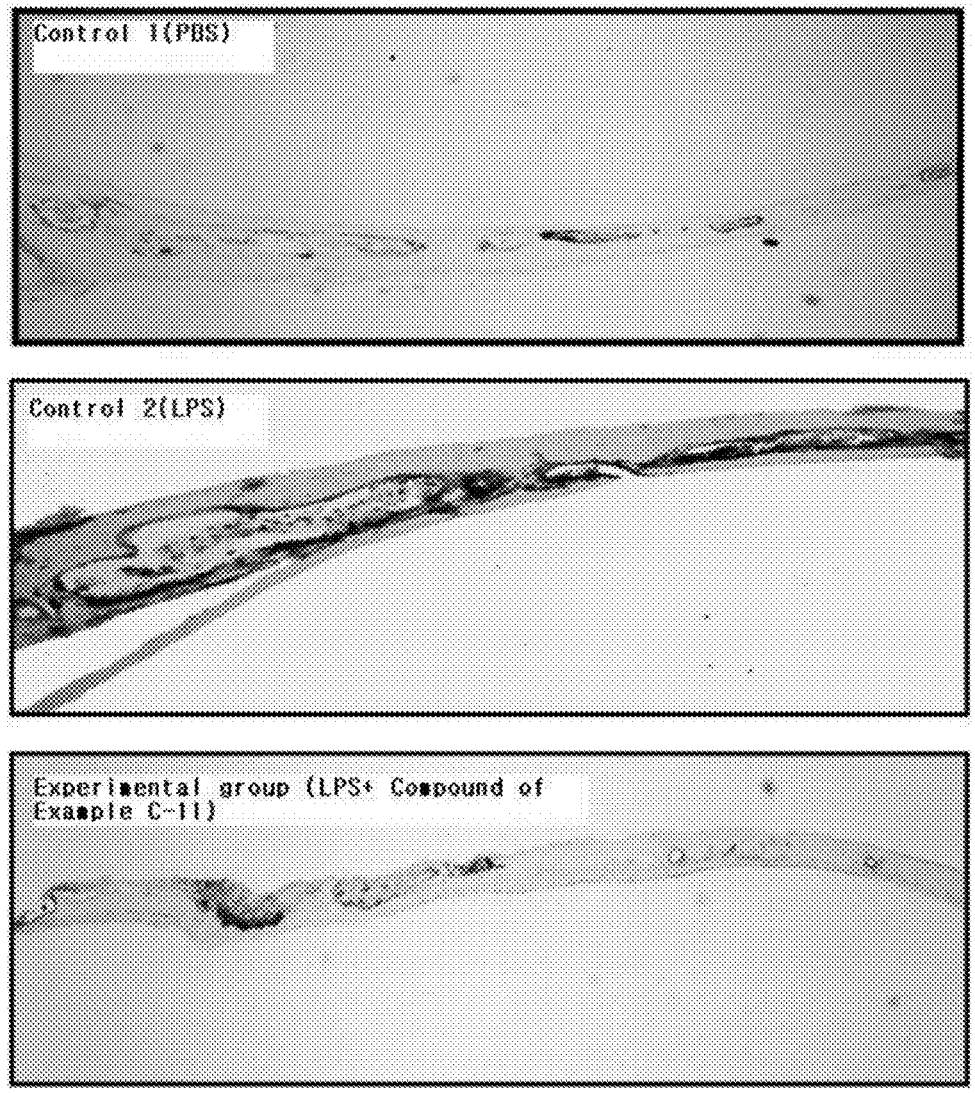

As shown in FIGS. 7 and 8, the experimental group with co-administration of the inventive compound and LPS exhibited a significantly smaller size of pores formed in bone, as compared to Control group 2 to which LPS alone was added.

From these results, it can be seen that the inventive compounds inhibit resorption of osteocytes by LPS, thereby suppressing osteolysis.

What is claimed is:
1. A compound of formula (I):

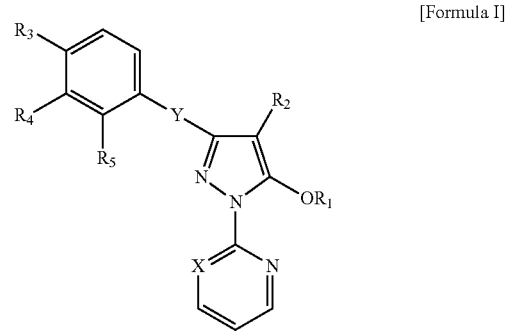

[Formula I]

wherein X represents —CH— or nitrogen;
Y represents —CH$_2$—, —CH$_2$CH$_2$—, —CH=CH—, —CH$_2$—O— or —O—CH$_2$—;
R$_1$ represents a hydrogen atom, an acetyl group, a tri(C$_1$-C$_4$) alkylsilanyl group, a diarylboranyl group or a (t-butoxy)carbamyl group;
R$_2$ represents a hydrogen atom or a C$_1$-C$_4$ alkyl group; and
R$_3$, R$_4$ and R$_5$ each independently represent a hydrogen atom, a hydroxyl group, a halogen atom, a (C$_6$-C$_{10}$) aryl group, a halo(C$_1$-C$_3$) alkyl group, a (C$_1$-C$_6$) alkoxy group, a tri(C$_1$-C$_4$) alkylsilaneoxy group or a benzodioxolyl group; or alternatively R$_3$ and R$_4$ or R$_4$ and R$_5$ taken together represent —CH$_2$—CH=CH—, —CH=CH—CH=CH— or —CH=CH—CH=CH—CH$_2$—; or a pharmaceutically acceptable salt thereof,
with the proviso that 3-benzyl-1-(pyridin-2-yl)-1H-pyrazol-5-ol is excluded.

2. The compound according to claim 1, wherein X represents —CH— or nitrogen; Y represents —CH$_2$—, —CH$_2$CH$_2$—, —CH=CH—, —CH$_2$—O— or —O—CH$_2$—; R$_1$ and R$_2$ represent a hydrogen atom; and R$_3$, R$_4$ and R$_5$ each independently represent a hydrogen atom, a hydroxyl group, a halogen atom, a ($C_6$-$C_{10}$) aryl group, a halo($C_1$-$C_3$) alkyl group, a ($C_1$-$C_6$) alkoxy group, a tri($C_1$-$C_4$) alkylsilaneoxy group or a benzodioxolyl group; or alternatively $R_3$ and $R_4$ or $R_4$ and $R_5$ taken together represent —$CH_2$—CH=CH— or —CH=CH—CH=CH—,
with the proviso that 3-benzyl-1-(pyridin-2-yl)-1H-pyrazol-5-ol is exclude.

3. The compound according to claim 2, wherein X represents —CH—; Y represents —CH=CH—, —$CH_2$—O— or —O—$CH_2$—; $R_1$ and $R_2$ represent a hydrogen atom; and $R_3$, $R_4$ and $R_5$ each independently represent a hydrogen atom, a hydroxyl group, a halogen atom, a halo($C_1$-$C_3$) alkyl group, a ($C_1$-$C_6$) alkoxy group or a tri($C_1$-$C_4$) alkylsilaneoxy group; or alternatively $R_3$ and $R_4$ or $R_4$ and $R_5$ taken together represent —CH=CH—CH=CH—.

4. The compound according to claim 3, wherein Y represents trans—CH=CH—.

5. The compound according to claim 1, wherein the compound is a compound selected from:
3-(o-bromobenzyl)-1-(pyridin-2-yl)-1H-pyrazol-5-ol,
3-(p-methoxybenzyl)-1-(pyridin-2-yl)-1H-pyrazol-5-ol,
3-(p-chlorobenzyl)-1-(pyridin-2-yl)-1H-pyrazol-5-ol,
3-phenethyl-1-(pyridin-2-yl)-1H-pyrazol-5-ol,
3-(phenoxymethyl)-1-(pyridin-2-yl)-1H-pyrazol-5-ol,
3-(naphthalen-3-yloxy)methyl)-1-(pyridin-2-yl)-1H-pyrazol-5-ol,
3-((4-chlorophenoxy)methyl)-1-(pyridin-2-yl)-1H-pyrazol-5-ol,
3-((2,4-dichlorophenoxy)methyl)-1-(pyridin-2-yl)-1H-pyrazol-5-ol,
1-(pyridin-2-yl)-3-styryl-1H-pyrazol-5-ol,
3-(4-methoxystyryl)-1-(pyridin-2-yl)-1H-pyrazol-5-ol,
3-(3,4-dimethoxystyryl)-1-(pyridin-2-yl)-1H-pyrazol-5-ol,
3-(3,4-dichlorostyryl)-1-(pyridin-2-yl)-1H-pyrazol-5-ol,
3-(4-i-propylstyryl)-1-(pyridin-2-yl)-1H-pyrazol-5-ol,
3-(4-trifluoromethylstyryl)-1-(pyridin-2-yl)-1H-pyrazol-5-ol,
3-(4-tert-butyldimethylsilyloxystyryl)-1-(pyridin-2-yl)-1H-pyrazol-5-ol,
3-(3-methoxy-4-tert-butyldimethylsilyloxystyryl)-1-(pyridin-2-yl)-1H -pyrazol-5-ol,
3-(3,5-dimethoxy-4-tert-butyldimethylsilyloxystyryl)-1-(pyridin-2-yl)-1H -pyrazol-5-ol,
3-(3-methoxy-4-tert-butyldimethylsilyloxystyryl)-1-(pyridin-2-yl)-1H -pyrazole-5-thiol,
3-(4-hydroxystyryl)-1-(pyridin-2-yl)-1H-pyrazol-5-ol,
3-(3-methoxy-4-hydroxystyryl)-1-(pyridin-2-yl)-1H-pyrazol-5-ol,
3-(3,5-dimethoxy-4-hydroxystyryl)-1-(pyridin-2-yl)-1H-pyrazol-5-ol,
3-(3-methoxy-4-hydroxystyryl)-1-(pyridin-2-yl)-1H-pyrazole-5-thiol, and
4-((E)-2-(5-amino-1-(pyridin-2-yl)-1H-pyrazol-3-yl)vinyl)-2-methoxyphenol; or a pharmaceutically acceptable salt thereof.

6. The compound according to claim 5, wherein the compound is a compound selected from:
3-phenethyl-1-(pyridin-2-yl)-1H-pyrazol-5-ol,
3-(p-chlorobenzyl)-1-(pyridin-2-yl)-1H-pyrazol-5-ol,
3-(phenoxymethyl)-1-(pyridin-2-yl)-1H-pyrazol-5-ol,
3-(naphthalen-3-yloxy)methyl)-1-(pyridin-2-yl)-1H-pyrazol-5-ol,
3-((2,4-dichlorophenoxy)methyl)-1-(pyridin-2-yl)-1H-pyrazol-5-ol,
1-(pyridin-2-yl)-3-styryl-1H-pyrazol-5-ol,
3-(4-methoxystyryl)-1-(pyridin-2-yl)-1H-pyrazol-5-ol,
3-(3,4-dimethoxystyryl)-1-(pyridin-2-yl)-1H-pyrazol-5-ol,
3-(3,4-dichlorostyryl)-1-(pyridin-2-yl)-1H-pyrazol-5-ol,
3-(4-trifluoromethylstyryl)-1-(pyridin-2-yl)-1H-pyrazol-5-ol,
3-(4-tert-butyldimethylsilyloxystyryl)-1-(pyridin-2-yl)-1H-pyrazol-5-ol,
3-(4-hydroxystyryl)-1-(pyridin-2-yl)-1H-pyrazol-5-ol, and
3-(3-methoxy-4-hydroxystyryl)-1-(pyridin-2-yl)-1H-pyrazole-5-thiol; or a pharmaceutically acceptable salt thereof.

7. A method for preparing a compound of formula (I), comprising heating a compound of formula (II) and 2-hydrazinopyridine in a polar organic solvent:

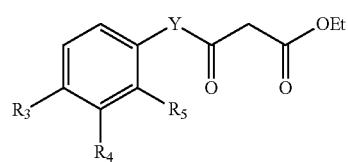

[Formula II]

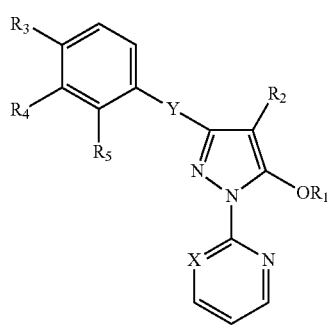

[Formula I]

wherein X represents —CH—;
Y represents —$CH_2$—, —$CH_2CH_2$—, —CH=CH—, —$CH_2$—O— or —$CH_2$—;
$R_1$ represents a hydrogen atom, an acetyl group, a tri($C_1$-$C_4$) alkylsilanyl group, a diarylboranyl group or a (t-butoxy)carbamyl group;
$R_2$ represents a hydrogen atom or a $C_1$-$C_4$ alkyl group; and
$R_3$, $R_4$ and $R_5$ each independently represent a hydrogen atom, a hydroxyl group, a halogen atom, a ($C_6$-$C_{10}$) aryl group, a halo($C_1$-$C_3$) alkyl group, a ($C_1$-$C_6$) alkoxy group, a tri($C_1$-$C_4$) alkylsilaneoxy group or a benzodioxolyl group; or alternatively $R_3$ and $R_4$ or $R_4$ and $R_5$ taken together represent —$CH_2$—CH=CH—, —CH=CH—CH=CH— or —CH=CH—CH=CH—$CH_2$—,
with the proviso that 3-benzyl-1-(pyridin-2-yl)-1H-pyrazol-5-ol is excluded from the compound of formula I prepared according to this method.

8. The method according to claim 7, wherein X represents —CH— or nitrogen; Y represents —$CH_2$—, —$CH_2CH_2$—, —CH=CH—, —$CH_2$—O— or —O—$CH_2$—; $R_1$ and $R_2$ represent a hydrogen atom; and $R_3$, $R_4$ and $R_5$ each independently represent a hydrogen atom, a hydroxyl group, a halogen atom, a ($C_6$-$C_{10}$) aryl group, a halo($C_1$-$C_3$) alkyl group, a ($C_1$-$C_6$) alkoxy group, a tri($C_1$-$C_4$) alkylsilaneoxy group or a benzodioxolyl group; or alternatively $R_3$ and $R_4$ or $R_4$ and $R_5$ taken together represent —$CH_2$—CH=CH— or —CH=CH—CH=CH—,
with the proviso that 3-benzyl-1-(pyridin-2-yl)-1H-pyrazol-5-ol is excluded from the compound of formula I prepared according to this method.

9. The method according to claim 7, wherein the polar organic solvent is selected from $C_1$-$C_4$ alcohol, acetic acid and a mixture thereof.

10. The method according to claim 9, wherein the polar organic solvent is ethanol or acetic acid.

11. The method according to claim 7, wherein the heating is carried out at a temperature of 100 to 130° C.

12. The method according to claim 7, wherein the reaction is carried out for 2 to 72 hours.

13. A pharmaceutical composition for the treatment of osteoporosis, comprising a compound of formula (I) or a pharmaceutically acceptable salt thereof:

[Formula I]

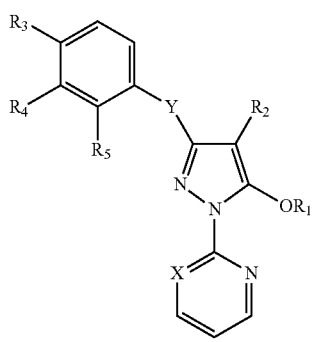

wherein X represents —CH— or nitrogen;
Y represents —$CH_2$—, —$CH_2CH_2$—, —CH=CH—, —$CH_2$—O— or —O—$CH_2$—;
$R_1$ represents a hydrogen atom, an acetyl group, a tri($C_1$-$C_4$) alkylsilanyl group, a diarylboranyl group or a (t-butoxy)carbamyl group:
$R_2$, represents a hydrogen atom or a $C_1$-$C_4$ alkyl group: and
$R_3$, $R_4$ and $R_5$ each independently represent a hydrogen atom, a hydroxyl group, a halogen atom, a ($C_6$-$C_{10}$) aryl group, a halo($C_1$-$C_3$) alkyl group, a ($C_1$-$C_6$) alkoxy group, a tri($C_1$-$C_4$) alkylsilaneox group or a benzodioxol group; or alternatively $R_3$ and $R_4$ or $R_4$ and $R_5$ taken together represent —$CH_2$—CH=CH—, —CH=CH—CH=CH— or —CH=CH—CH=CH—$CH_2$—.

14. The composition according to claim 13, wherein the osteoporosis is post-menopausal osteoporosis.

15. The composition according to claim 13, wherein the compound represented by formula (I) or a pharmaceutically acceptable salt thereof inhibits the generation of reactive oxygen species.

16. The composition according to claim 13, wherein the compound represented by formula (I) or a pharmaceutically acceptable salt thereof inhibits the production of osteoclasts.

17. A method for treating osteoporosis, comprising administering a composition containing a compound represented by formula (I) or a pharmaceutically acceptable salt thereof to a subject:

[Formula I]

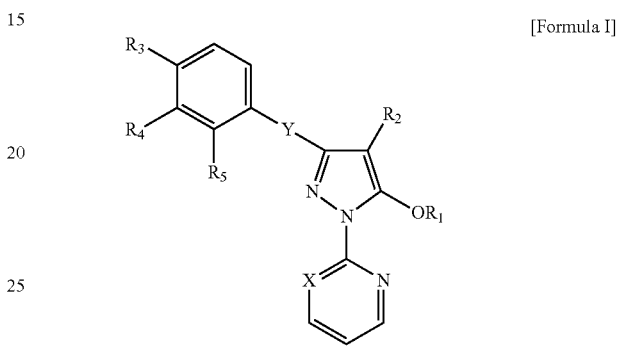

wherein X represents —CH— or nitrogen;
Y represents —$CH_2$—, —$CH_2CH_2$—, —CH=CH—, —$CH_2$—O— or —O—$CH_2$—;
$R_1$ represents a hydrogen atom, an acetyl group, a tri($C_1$-$C_4$) alkylsilanyl group, a diarylboranyl group or a (t-butoxy)carbamyl group;
$R_2$ represents a hydrogen atom or a $C_1$-$C_4$ alkyl group; and
$R_3$, $R_4$ and $R_5$ each independently represent a hydrogen atom, a hydroxyl group, a halogen atom, a ($C_6$-$C_{10}$) aryl group, a halo($C_1$-$C_3$) alkyl group, a ($C_1$-$C_6$) alkoxy group, a tri($C_1$-$C_4$) alkylsilaneoxy group or a benzodioxolyl group; or alternatively $R_3$ and $R_4$ or $R_4$ and $R_5$ taken together represent —$CH_2$—CH=CH—, —CH=CH—CH=CH— or —CH=CH—CH=CH—$CH_2$—.

* * * * *

UNITED STATES PATENT AND TRADEMARK OFFICE
CERTIFICATE OF CORRECTION

PATENT NO. : 8,637,674 B2
APPLICATION NO. : 13/393800
DATED : January 28, 2014
INVENTOR(S) : Yun Soo Bae et al.

It is certified that error appears in the above-identified patent and that said Letters Patent is hereby corrected as shown below:

In the claims

Column 31, Lines 6-7:
"with the proviso that 3-benzyl-1-(pyridine-2-yl)-1H-pyrazol-5-ol is exclude." should read, --with the proviso that 3-benzyl-1-(pyridine-2-yl)-1H-pyrazol-5-ol is excluded.--.

Column 31, Lines 41-42:
"3-(3-methoxy-4-tert-butyldimethylsilyloxystyryl)-1-(pyridine-2-yl)-1H -pyrazol-5-ol," should read, --3-(3-methoxy-4-tert-butyldimethylsilyloxystyryl)-1-(pyridine-2-yl)-1H-pyrazol-5-ol,--.

Column 31, Lines 43-44:
"3-(3,5-dimethoxy-4-tert-butyldimethylsilyloxystyryl)-1-(pyridin-2-yl)-1H -pyrazol-5-ol," should read, --3-(3,5-dimethoxy-4-tert-butyldimethylsilyloxystyryl)-1-(pyridin-2-yl)-1H-pyrazol-5-ol,--.

Column 31, Lines 45-46:
"3-(3-methoxy-4-tert-butyldimethylsilyoxystyryl)-1-(pyridine-2-yl)-1H -pyrazole-5-thiol," should read, --3-(3-methoxy-4-tert-butyldimethylsilyoxystyryl)-1-(pyridine-2-yl)-1H-pyrazole-5-thiol,--.

Column 32, Lines 39-40:
"Y represents $-CH_2-$, $-CH_2CH_2-$, $-CH=CH-$, $-CH_2-O-$ or $-CH_2-$;" should read, --Y represents $-CH_2-$, $-CH_2CH_2-$, $-CH=CH-$, $-CH_2-O-$ or $-O-CH_2-$;--.

Column 33, Line 7:
"is carried out at a temperature of 100to 130° C." should read, --is carried out at a temperature of 100 to 130° C.--.

Signed and Sealed this
Sixth Day of October, 2015

Michelle K. Lee
*Director of the United States Patent and Trademark Office*

CERTIFICATE OF CORRECTION (continued)
U.S. Pat. No. 8,637,674 B2

In the claims

Column 33, Line 36:
"$R_2$, represents a hydrogen atom or a $C_1$-$C_4$ alkyl group: and" should read, --$R_2$ represents a hydrogen atom or a $C_1$-$C_4$ alkyl group; and--.

Column 33, Line 40:
"group, a tri($C_1$-$C_4$) alkysilaneox group or a benzodioxol" should read, --group, a tri($C_1$-$C_4$) alkysilaneoxy group or a benzodioxolyl--.